(12) United States Patent
Menn

(10) Patent No.: US 9,918,715 B2
(45) Date of Patent: Mar. 20, 2018

(54) ARTICULATING STEERABLE CLIP APPLIER FOR LAPAROSCOPIC PROCEDURES

(71) Applicant: Conmed Corporation, Utica, NY (US)

(72) Inventor: Pavel Menn, Marblehead, MA (US)

(73) Assignee: Conmed Corporation, Utica, NY (US)

( * ) Notice: Subject to any disclaimer, the term of this patent is extended or adjusted under 35 U.S.C. 154(b) by 903 days.

(21) Appl. No.: 14/339,021

(22) Filed: Jul. 23, 2014

(65) Prior Publication Data

US 2014/0336675 A1   Nov. 13, 2014

Related U.S. Application Data

(63) Continuation of application No. 13/080,998, filed on Apr. 6, 2011, now abandoned.

(60) Provisional application No. 61/321,233, filed on Apr. 6, 2010.

(51) Int. Cl.
 *A61B 17/10* (2006.01)
 *A61B 17/128* (2006.01)
 *A61B 17/00* (2006.01)

(52) U.S. Cl.
 CPC .......... *A61B 17/10* (2013.01); *A61B 17/1285* (2013.01); *A61B 2017/00314* (2013.01); *A61B 2017/00323* (2013.01)

(58) Field of Classification Search
 CPC . A61B 17/00234; A61B 17/068; A61B 17/10; A61B 17/128; A61B 17/1285; A61B 2017/003; A61B 2017/00314
 USPC ....................................................... 606/142
 See application file for complete search history.

(56) References Cited

U.S. PATENT DOCUMENTS

| 3,266,059 A | 8/1966 | Stelle |
| 5,174,277 A | 12/1992 | Matsumaru |
| 5,454,827 A * | 10/1995 | Aust ...................... A61B 17/29 |
| | | 600/564 |

(Continued)

FOREIGN PATENT DOCUMENTS

WO   2011/127137   10/2011

OTHER PUBLICATIONS

Office Action for U.S. Appl. No. 13/080,998, dated Jan. 24, 2014, 10 pages.

(Continued)

*Primary Examiner* — Melanie Tyson
(74) *Attorney, Agent, or Firm* — Frederick JM Price; Bond, Schoeneck & King, PLLC

(57) ABSTRACT

A long articulating steerable clip applier affixed to a user-operated handle. A surgical jaw assembly is attached to the other end of the clip applier. The clip applier is composed of articulating phalanges that are connected end to end by pivoting links and capable of angulations relative to one another when subjected to a tensile force. Each phalange has opposing s-shaped exterior grooves that form two continuous spiral-shaped channels for holding tension wires once the phalanges are assembled. Multiple tension wires are attached to opposite ends of adjacent phalanges. When each wire is pulled, this tensile force causes the phalanges to pivot at equivalent angles with each other. As each individual phalange pivots by an equivalent angle, the sum of these angles causes the free end of the clip applier to pivot by a large angle or a cascading actuation effect.

17 Claims, 19 Drawing Sheets

(56) References Cited

U.S. PATENT DOCUMENTS

| | | |
|---|---|---|
| 5,556,370 A | 9/1996 | Maynard |
| 5,562,682 A | 10/1996 | Oberlin et al. |
| 5,601,573 A | 2/1997 | Fogelberg et al. |
| 5,626,585 A | 5/1997 | Mittelstadt et al. |
| 5,681,263 A | 10/1997 | Flesch |
| 5,749,828 A | 5/1998 | Solomon et al. |
| 5,755,726 A | 5/1998 | Pratt et al. |
| 5,833,696 A | 11/1998 | Whitfield et al. |
| 6,248,062 B1 | 6/2001 | Adler et al. |
| 6,364,828 B1 | 4/2002 | Yeung et al. |
| 6,705,989 B2 | 3/2004 | Cuschieri et al. |
| 6,869,435 B2 | 3/2005 | Blake, III |
| 6,936,042 B2 | 8/2005 | Wallace et al. |
| 6,942,613 B2 | 9/2005 | Ewers et al. |
| 7,250,027 B2 | 7/2007 | Barry |
| 7,297,149 B2 | 11/2007 | Vitali et al. |
| 7,585,304 B2 | 9/2009 | Hughett |
| 7,766,821 B2 | 8/2010 | Brunnen et al. |
| 7,874,980 B2 | 1/2011 | Sonnenschein et al. |
| 7,942,885 B2 | 5/2011 | Sixto, Jr. et al. |
| 8,292,905 B2 | 10/2012 | Taylor et al. |
| 8,403,945 B2 | 3/2013 | Whitfield et al. |
| 8,465,420 B2 | 6/2013 | Ostrovsky et al. |
| 2004/0044270 A1 | 3/2004 | Barry |
| 2005/0197536 A1 | 9/2005 | Banik et al. |
| 2005/0272978 A1 | 12/2005 | Brunnen et al. |
| 2006/0178560 A1 | 8/2006 | Saadat et al. |
| 2008/0132761 A1 | 6/2008 | Sonnenschein et al. |
| 2008/0287741 A1 | 11/2008 | Ostrovsky et al. |
| 2010/0010512 A1 | 1/2010 | Taylor et al. |
| 2012/0265220 A1 | 10/2012 | Menn |
| 2013/0172912 A1 | 7/2013 | Whitfield et al. |

OTHER PUBLICATIONS

Office Action for U.S. Appl. No. 13/080,998, dated May 28, 2013, 6 pages.

International Search Report for International Application No. PCT/US2011/031373, dated Jun. 17, 2011.

Written Opinion of the International Search Authority for International Application No. PCT/US2011/031373 dated Jun. 17, 2011.

International Preliminary Report on Patentability Chapter I for International Application No. PCT/US2011/031373, dated Oct. 9, 2012.

* cited by examiner

ARTICULATING STEERABLE CLIP APPLIER FOR LAPAROSCOPIC PROCEDURES

CROSS REFERENCE TO RELATED APPLICATION

This application is a continuation of U.S. patent application Ser. No. 13/080,998 filed Apr. 6, 2011, now abandoned, which claims the benefit of U.S. Provisional Application No. 61/321,233 filed on Apr. 6, 2010, the entire contents of which are incorporated herein by reference.

FIELD OF THE INVENTION

This invention relates to a novel articulating steerable clip applier for laparoscopic or endoscopic procedures.

BACKGROUND OF INVENTION

Laparoscopic and endoscopic procedures are conducted through a small incision in the skin or natural body orifices.

In order to operate on a given tissue or a blood vessel, surgeons must ligate or occlude blood vessels to prevent patient blood loss. Surgical clip appliers are used in these surgeries for the application of hemostatic clips to ligate vessels. Clip appliers hold a surgical clip in an open position in a pair of specially adapted jaws. Once these jaws, containing clips, are positioned over a vessel, the clip is manually released over the vessel to ligate it. Inaccuracies in movement or failure to securely occlude the clip to the vessel can result damage to vessels or tissues, internal bleeding, lethal drops in blood pressure, infections, or longer recovery periods These instruments need to provide precise and accurate movement in order to ligate vessels within the body that are difficult to access. Instruments are needed that are narrow enough to be inserted through a small opening (such as an incision, trocar or natural body orifice), long enough to reach the desired internal tissues, and flexible enough to provide a wide range of motion to navigate the distal end of a clip applier with jaws containing loaded clips around body tissues to advance towards the internal operation site.

Accordingly, the subject invention discloses an improved steerable articulating surgical clip applier. It contains a long, narrow, distal articulating disposable portion that is inserted into a patient during surgery. This distal articulating portion is removably attached to a proximal non-disposable control unit for moving the long disposable portion within the patient and operating actuators to control the articulation and ligation of the clip applier.

By separating these two components, the risk of cross contamination between separate patients or separate tissues on the same patient is reduced. The non-disposable control unit does not enter the patient and the contaminated long and narrow component is simply disposed after each surgical procedure is completed. In addition, costs are saved since medical providers only need to replace the disposable component between surgical procedures.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses an endoscopic surgical tool having a handle and a shaft member coupled to the handle and extending along a shaft axis from a proximal end to a distal end, wherein the distal end of the shaft member is adapted to receive an end effector, comprising: A. a linear array of n phalanx sections, where n is an integer greater than 2, wherein the linear array includes a sequentially aligned proximal phalanx section, n−2 intermediate phalanx sections, and a distal phalanx section, wherein the ith phalanx section, wherein i is greater than or equal to 1 and less than or equal to n, extends along an associated central axis $CA_i$ between a proximal end $PE_i$ and a distal end $DE_i$, and includes: a tubular member $TM_i$ defining a. a central void region $CVR_i$ extending along the central axis $CA_i$ between the proximal end $PE_i$ and the distal end $DE_i$, and b. an exterior surface $ES_i$ disposed about the central void region $CVR_i$ and extending along the central axis $CA_i$ from the proximal end $PE_i$ to the distal end $DE_i$, wherein the n phalanx sections are aligned whereby the central axis $CA_i$ of each phalanx section intersects with the central axis of phalanx sections adjacent thereto in the linear array, B. an end effector coupler EEC disposed at the distal end of the distal phalanx section and adapted for coupling the distal end to an end effector, C. a base coupling assembly BC disposed at the proximal end of the proximal phalanx section and adapted to couple to the proximal end of the proximal phalanx section to the distal end of the shaft member, whereby the shaft axis intersects the central axis of the proximal phalanx section and whereby the proximal phalanx section is movable with respect to the distal end of the shaft member substantially only in rotational motion about a transverse axis $TA_0$ perpendicular to the central axis of the proximal phalanx section, D. n−1 phalanx section coupling assemblies PC, wherein each phalanx section coupling assembly is associated with an intermediate phalanx section and wherein the coupling assembly $PC_i$ associated with the ith phalanx section couples a distal end of the ith phalanx section to the proximal end of the adjacent i+1th phalanx section whereby the proximal end of the i+1th phalanx section is movable with respect to the distal end of the ith phalanx section substantially only in rotational motion about a transverse axis $TA_i$ perpendicular to the central axis of the ith phalanx section, wherein $TA_i$ and $TA_0$ are mutually parallel, and wherein each of the base coupling assembly and the n−1 phalanx coupling assemblies are operative whereby a torque applied to the proximal end of the proximal phalanx section about an axis parallel to transverse axis $TA_0$, effects a same-direction angular rotational displacement of each of the ith phalanx sections with respect to the adjacent phalanx sections about the respective transverse axes $TA_i$.

In a further embodiment of the subject invention, the base coupling assembly BC may be adapted to detachably couple the proximal end of the proximal phalanx section to the distal end of the shaft member.

In another embodiment of the subject invention, the end effector coupling assembly EEC may be adapted to detachably couple the end effector to the distal end of the distal phalanx section.

In an additional embodiments of the subject invention, the ith phalanx section coupling assembly $C_i$ may include: i. a coupling cam surface $CCS_i$ disposed about a cam central axis $CCA_i$ affixed to the distal end of the ith phalanx section, wherein the cam central axis $CCA_i$ is substantially coaxial with the transverse axis $TA_i$, a substantially non-stretchable link coupling a point on the coupling cam surface of the ith phalanx section $CCSP_i$ with a point $EP_{i+2}$ on the proximal end of the i+2th phalanx section, wherein point $CCSP_i$ and point $EP_i$ are disposed in a plane including $CA_{i+1}$ and perpendicular to the transverse axes $TA_i$ and $TA_{i+2}$ and on opposite sides central axis of the i+1 phalanx section $CA_{i+1}$.

In a further embodiment of the subject invention, the link of coupling assembly $C_i$ may be a cable extending between point $CCSP_i$ and point $EP_{i+2}$.

In another embodiment of the subject invention, the cable extends in a helical path about the central axis $CA_{i+1}$ between point $CCSP_i$ and point $EP_{i+2}$.

In an additional embodiment of the subject invention, the exterior surface $ES_i$ includes an open-faced helical channel $HC_{i+1}$ disposed about the central axis $CA_{i+1}$, and the cable of coupling assembly $C_i$ extends through the helical channel $HC_{i+1}$.

In a further embodiment of the subject invention, the same-direction angular rotational displacement of each of the ith phalanx sections with respect to the adjacent phalanx sections are equi-angle.

In another embodiment of the subject invention, the tubular members $TM_i$ may be characterized by the same distance between the proximal end $PE_i$ and the distal end $De_i$.

In a further embodiment of the subject invention, at least two of the tubular members $TM_i$ may be characterized by different distances between their respective proximal ends $PE_i$ and distal ends $De_i$.

In an additional embodiment of the subject invention, the cam surfaces $CCS_i$ may be circular segments.

The subject invention also discloses an endoscopic surgical apparatus comprising: a handle having a front end and defining a longitudinal axis; an actuation member associated with the handle; an elongated articulating section comprising a plurality of interconnected pivotable vertebrae extending distally from the front end of said handle, wherein the plurality of pivotable vertebrae comprises an exterior surface, further wherein the plurality of pivotable vertebrae comprises an interior surface that defines a channel extending distally from the front end of said handle to a distal end to permit passage of surgical clips; and a tensioning system selectively operable from the actuation member to apply tensioning force to the plurality of interconnected pivotable vertebrae such that the proximal end of each interconnected pivotable vertebrae pivots at a substantially equivalent angle.

Another embodiment of the subject invention is an endoscopic surgical apparatus comprising: a handle having a front end and defining a longitudinal axis; an actuation member associated with the handle; an elongated articulating section comprising a plurality of interconnected pivotable vertebrae extending distally from the front end of said handle, wherein the plurality of pivotable vertebrae comprises an exterior surface, wherein each pivotable vertebrae comprises a set of opposing spiral-shaped grooves on the exterior surface such that the elongated articulating section has contiguous set of opposing spiral-shaped grooves, further wherein the plurality of pivotable vertebrae comprises an interior surface that defines a channel extending distally from the front end of said handle to a distal end to permit passage of surgical clips; and a plurality of tension wires inserted into the contiguous spiral-shaped grooves, wherein the plurality of tension wire are selectively operable from the actuation member to apply tensioning force to the plurality of interconnected pivotable vertebrae such that the proximal end of each interconnected pivotable vertebrae pivots at a substantially equivalent angle.

An additional embodiment of the subject invention is an endoscopic surgical apparatus comprising: a handle having a front end and defining a longitudinal axis; an actuation member associated with the handle; an elongated articulating section comprising a plurality of interconnected pivotable vertebrae extending distally from the front end of said handle, wherein the plurality of pivotable vertebrae comprises an exterior surface, wherein each pivotable vertebrae comprises a set of opposing spiral-shaped grooves on the exterior surface such that the elongated articulating section has contiguous set of opposing spiral-shaped grooves, further wherein the plurality of pivotable vertebrae comprises an interior surface that defines a channel extending distally from the front end of said handle to a distal end to permit passage of surgical clips; and a plurality of tension wires inserted into the contiguous spiral-shaped grooves, wherein the plurality of tension wire are selectively operable from the actuation member to apply tensioning force to the plurality of interconnected pivotable vertebrae such that the proximal end of each interconnected pivotable vertebrae pivots at a substantially equivalent angle.

A further embodiment of the subject invention discloses an endoscopic surgical apparatus comprising: a handle having a front end and defining a longitudinal axis; an actuation member associated with the handle; an elongated articulating section comprising a plurality of interconnected pivotable vertebrae extending distally from the front end of said handle, wherein the plurality of pivotable vertebrae comprises an exterior surface, further wherein the plurality of pivotable vertebrae comprises an interior surface that defines a channel extending distally from the front end of said handle to a distal end to permit passage of surgical clips; and a plurality of semi-circular ligaments placed over the plurality of pivotable vertebrae, wherein the plurality of semi-circular ligaments are selectively operable from the actuation member to apply tensioning force to the plurality of interconnected pivotable vertebrae such that the proximal end of each interconnected pivotable vertebrae pivots at a substantially equivalent angle.

Another embodiment of the subject invention is an endoscopic surgical apparatus comprising: a handle having a front end and defining a longitudinal axis; an actuation member coupled with the handle; an elongated articulating shaft coupled to the handle with a base coupling assembly and extending distally from the front end of said handle from a proximal end to a distal end, wherein the distal end of the articulating shaft is adapted to receive an end effector, the articulating shaft comprising a linear array of phalanx sections, wherein the linear array includes a sequentially aligned proximal phalanx section coupled on a distal end to the base coupling assembly, intermediate phalanx sections, and a distal phalanx section adapted to receive the end effector on the distal end, wherein each phalanx section comprises i) a proximal end and a distal end; ii) a central cavity extending along a central axis between the proximal end and the distal end; iii) an exterior surface; and iv) a set of opposing substantially spiral-shaped grooves on the exterior surface that extend along each phalanx from the proximal end to the distal end, wherein each the distal end of each phalanx section couples the proximal end of the adjacent phalanx section, whereby the proximal end of the phalanx section is movable with respect to the distal end of the phalanx section in rotational motion, and a plurality of tension wires inserted into the spiral-shaped grooves, wherein the plurality of tension wire are operable from the actuation member to apply tensioning force to the linear array of phalanx sections such that the proximal end of each phalanx section pivots at a substantially equivalent angle.

Another embodiment of the subject invention is an endoscopic surgical apparatus comprising: a handle having a front end and defining a longitudinal axis; an actuation member coupled with the handle; an elongated articulating shaft coupled to the handle with a base coupling assembly and extending distally from the front end of said handle from a proximal end to a distal end, wherein the distal end of the articulating shaft is adapted to receive an end effector, the articulating shaft comprising a linear array of phalanx sections, wherein the linear array includes a sequentially aligned proximal phalanx section coupled on a distal end to the base coupling assembly, intermediate phalanx sections, and a distal phalanx section adapted to receive the end effector on the distal end, wherein each phalanx section comprises i) a proximal end and a distal end; ii) a central cavity extending along a central axis between the proximal end and the distal end; iii) an exterior surface; wherein each the distal end of each phalanx section couples the proximal end of the adjacent phalanx section, whereby the proximal end of the phalanx section is movable with respect to the distal end of the phalanx section in rotational motion, and a plurality of semi-cylindrical ligaments placed over the plurality of phalanx sections, wherein the plurality of semi-cylindrical ligaments are selectively operable from the actuation member to apply tensioning force to the plurality of phalanx sections such that the proximal end of each phalanx section pivots at a substantially equivalent angle.

In embodiments of the subject invention, each phalanx or pivotable vertebrae may comprise a substantially cylindrical configuration.

In other embodiments of the subject invention, each phalanx or pivotable vertebrae may comprise a single piece.

In further embodiments of the subject invention, each phalanx or pivotable vertebrae may comprise two substantially half-cylindrical pieces.

In additional embodiments of the subject invention, the elongated articulating section may further comprise a distally attached surgical jaws assembly. In another embodiment the subject invention, the end effector may comprise a distally attached surgical jaws assembly.

In other embodiments of the subject invention, each pivotable vertebrae may project a first pivot member from the proximal end and project a second pivot member from the distal end, wherein the first pivot member of each pivotable vertebrae pivotably couples about a rotational axis to the second pivot member of a proximally adjacent pivotable vertebrae.

In further embodiments of the subject invention, the first pivot member may comprise a substantially cylindrical protrusion and the second pivot member may comprise a substantially cylindrical bore adapted for receiving the substantially cylindrical protrusion.

In other embodiments of the subject invention, each pivotable vertebrae may project a plurality of first pivot members from the proximal end and project a plurality of second pivot members from the distal end, wherein the plurality of first pivot members of each pivotable vertebrae pivotably couples about a rotational axis to the plurality of second pivot members of proximally adjacent pivotable vertebrae.

In additional embodiments of the subject invention, each phalanx section or pivotable vertebrae may be composed of injected-molded plastic.

In embodiments of the subject invention, the plurality of pivotable vertebrae fits within 3 mm to 10 mm envelope of MIS instrumentation.

In other embodiments of the subject invention, the plurality of tension wire may comprise a material selected from the group consisting of nickel titanium alloy, braided stainless steel, a single stainless steel wire, Kevlar, a high tensile strength monofilament thread, or combinations thereof.

In further embodiments of the subject invention, each tension wire attaches on a proximal end to a pivotable vertebrae proximate to the handle, extends through the spiral shaped grooves on a first subsequent adjacent distal pivotable vertebrae, and attaches on a distal end to a second subsequent adjacent distal pivotable vertebrae.

In additional embodiments of the subject invention, each tension wire proximally attaches on one side of the elongated articulating section to a pivotable vertebrae proximate to the handle, extends through the spiral shaped grooves on a subsequent adjacent distal pivotable vertebrae, and distally attaches on the opposing side of elongated articulating section to an opposing side of second subsequent adjacent distal pivotable vertebrae.

In other embodiments of the subject invention, applying force in the proximal direction to the proximal end of each tension wire rotates the second subsequent adjacent distal pivotable vertebrae, further wherein the direction of rotation is away from the side on the elongated articulating section that attaches to the proximal end of the tension wire.

In embodiments of the subject invention, applying force in the proximal direction to the proximal end of each tension wire rotates the second subsequent adjacent distal pivotable vertebrae, further wherein the direction of rotation is toward the side on the elongated articulating section that attaches to the distal end of the tension wire.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of embodiments thereof, which description should be considered in conjunction with the accompanying drawings, in which.

DETAILED DESCRIPTION OF THE EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

Figure 1:
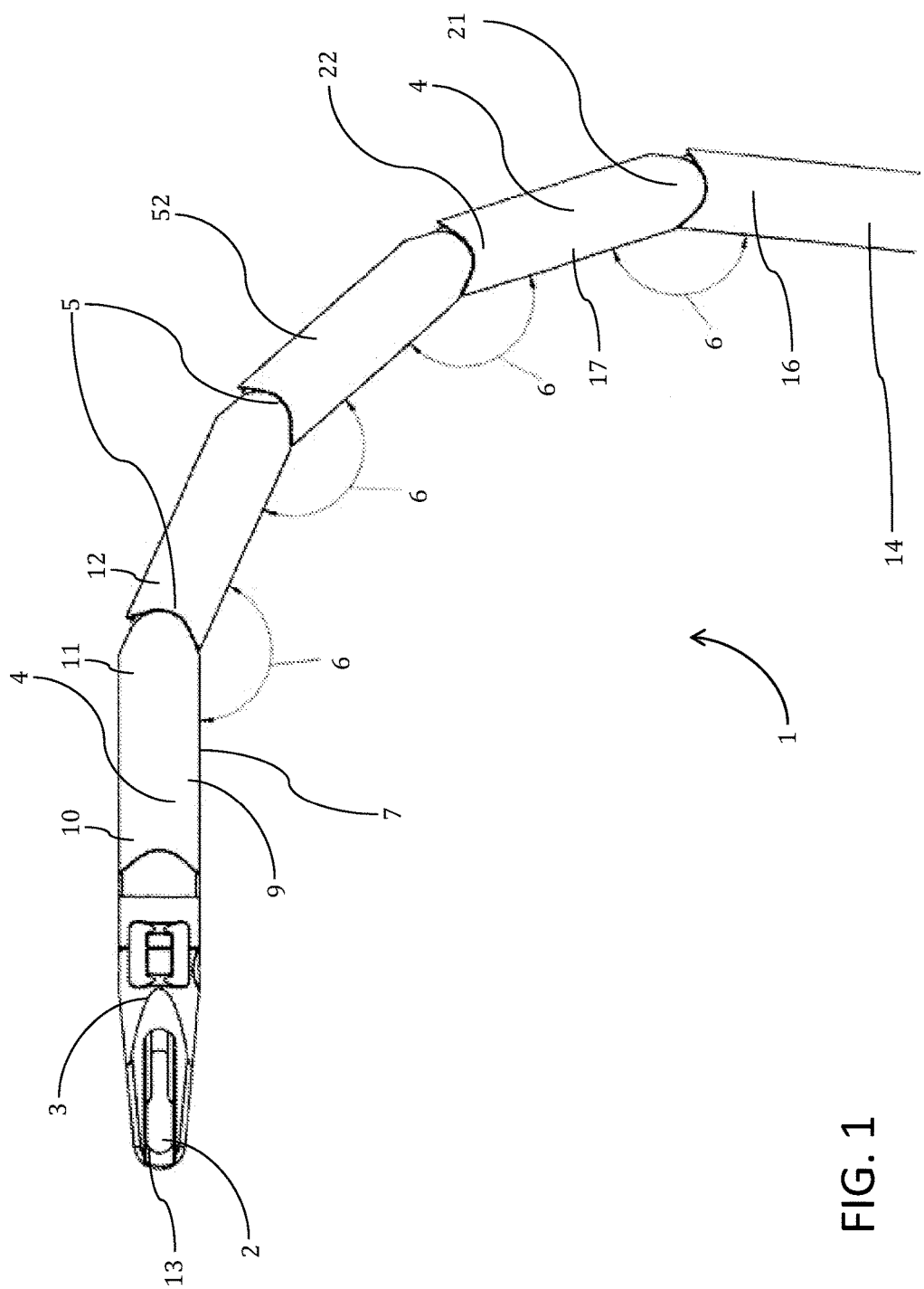
FIG. 1 illustrates a top view of the articulating steerable clip applier showing the separate angles of movement by different phalanges with covers.
Figure 2:
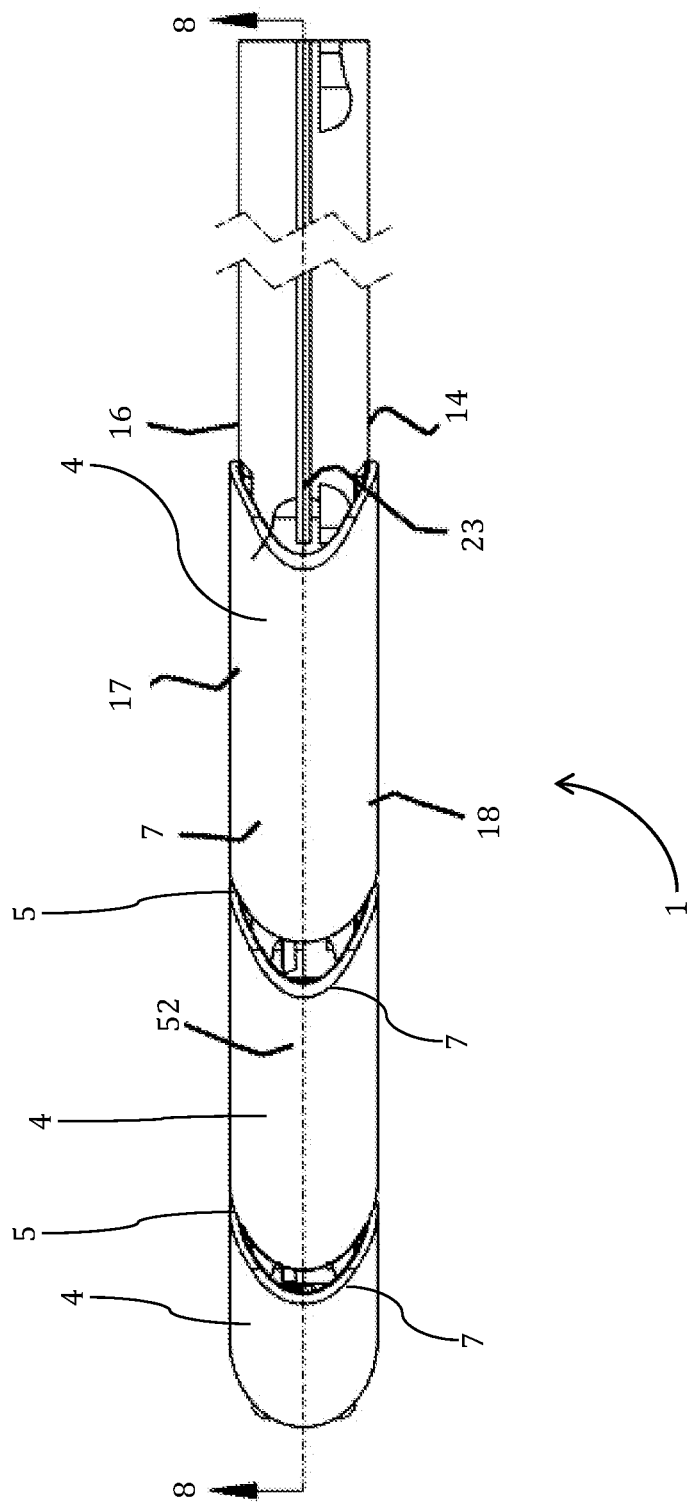
FIG. 2 illustrates a side view of the articulating steerable clip applier showing the separate angles of movement by different phalanges within a cover.
Figure 3:
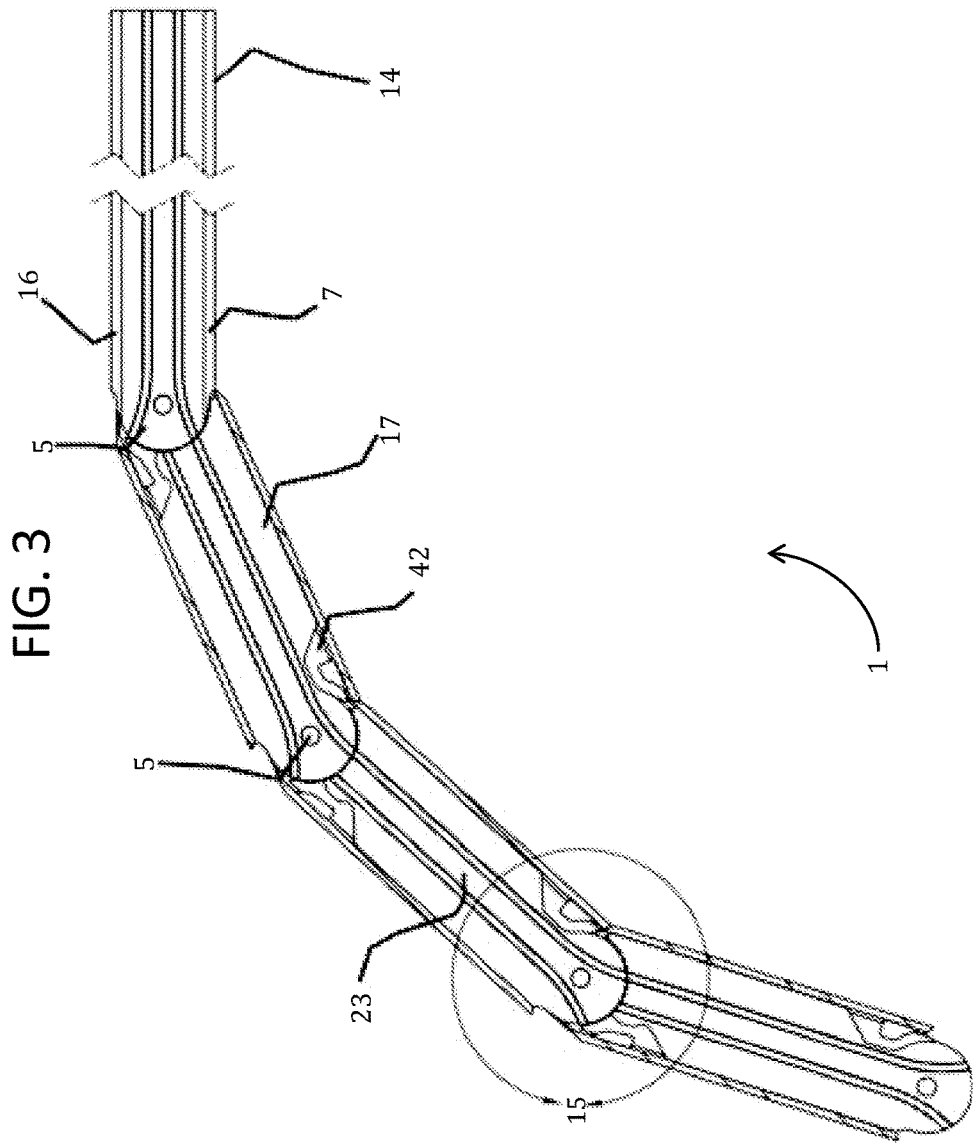
FIG. 3 illustrates a cross-sectional top view of the articulating steerable clip applier along the line 8 of FIG. 2.
Figure 4:
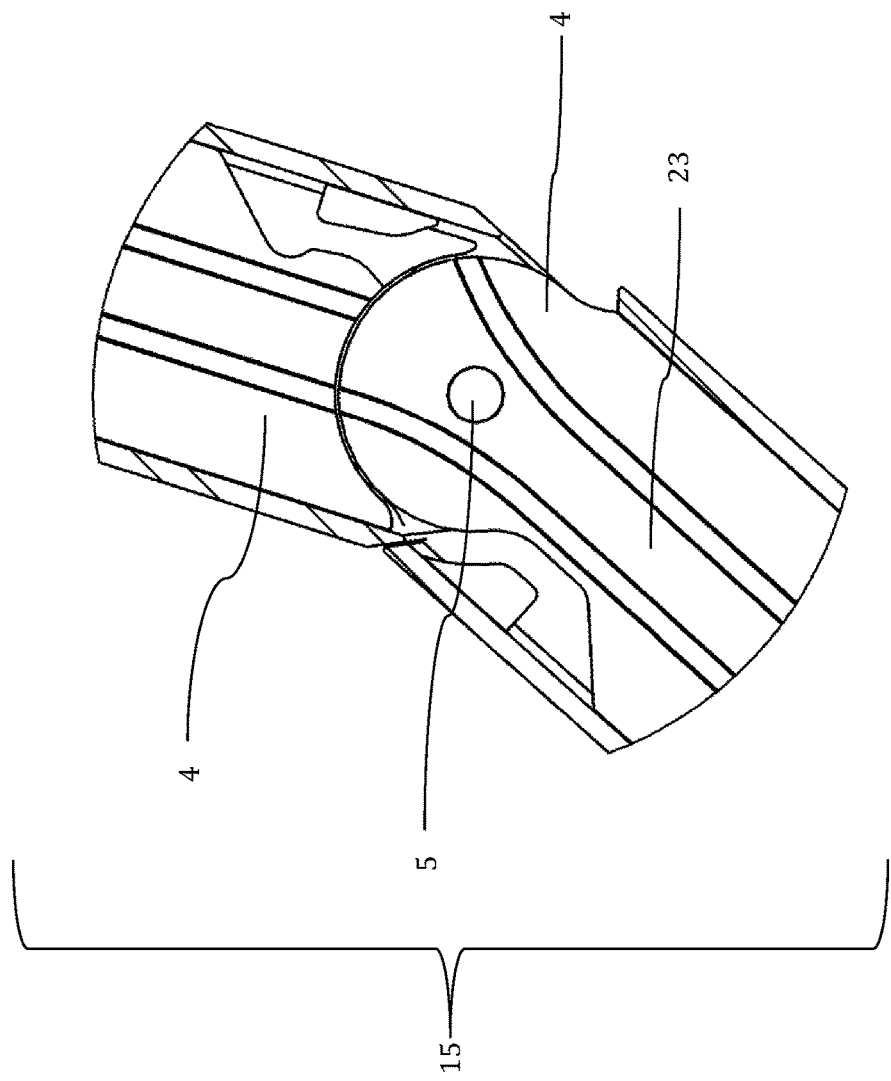
FIG. 4 illustrates an enlarged cross-sectional top view of line 15 of FIG. 3 showing the pivotable connection between two phalanges on the articulating steerable clip applier.
Figure 19:
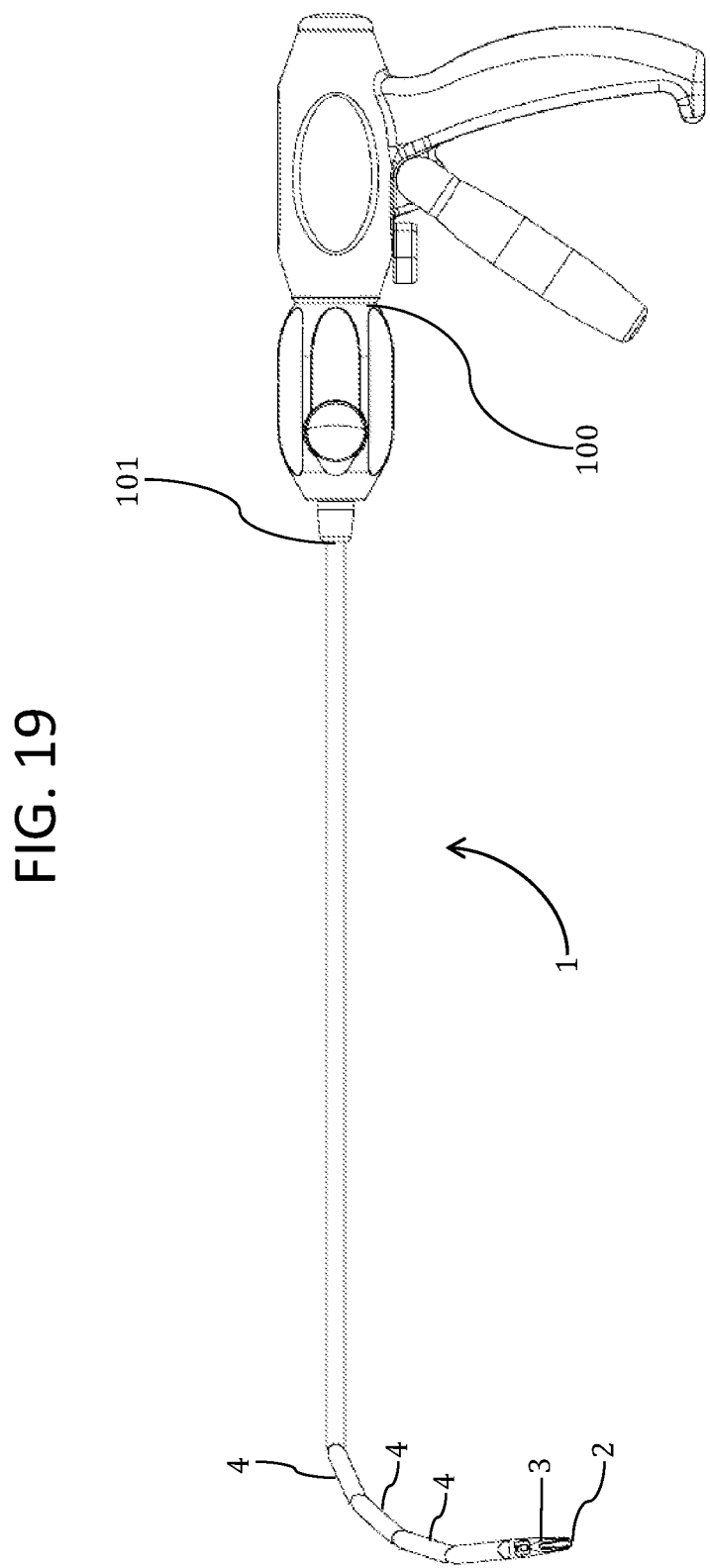
FIG. 19 illustrates a side view of an articulating steerable clip applier operatively attached on the proximal end to a user-operated handle.

FIGS. 1-3, 5, 6 and 11 illustrate a distal end 2 of the articulating steerable clip applier 1. The clip applier 1 is a long, narrow structure with a free distal end 2 adapted for coupling to an end effector, such as a surgical jaw assembly 3, and a proximal end 101 operatively coupled to a user-operated handle 100 (as shown in FIG. 19). The clip applier 1 is composed of a plurality of relatively short articulating members or phalanges 4 that are connected end to end by pivoting links 5 and capable of angulations 6 relative to one another when subjected to a tensile force. FIG. 3 illustrates a cross-sectional top view of the articulating steerable clip applier along the line 8 of FIG. 2. FIG. 4 illustrates an enlarged cross-sectional top view of pivoting point 5 showing the pivotable connection between two phalanges 4 on the articulating steerable clip applier 1 from line 15 of FIG. 3.

Figure 17:
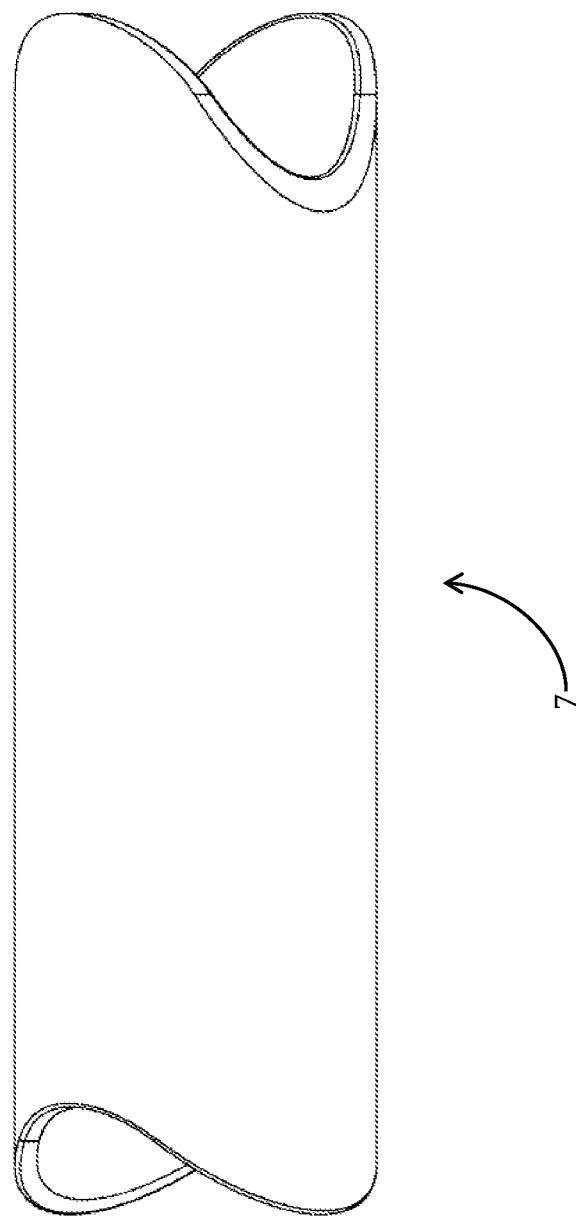
FIG. 17 illustrates a side view of a substantially circular elongate tubing that covers each individual phalange.
Figure 18:
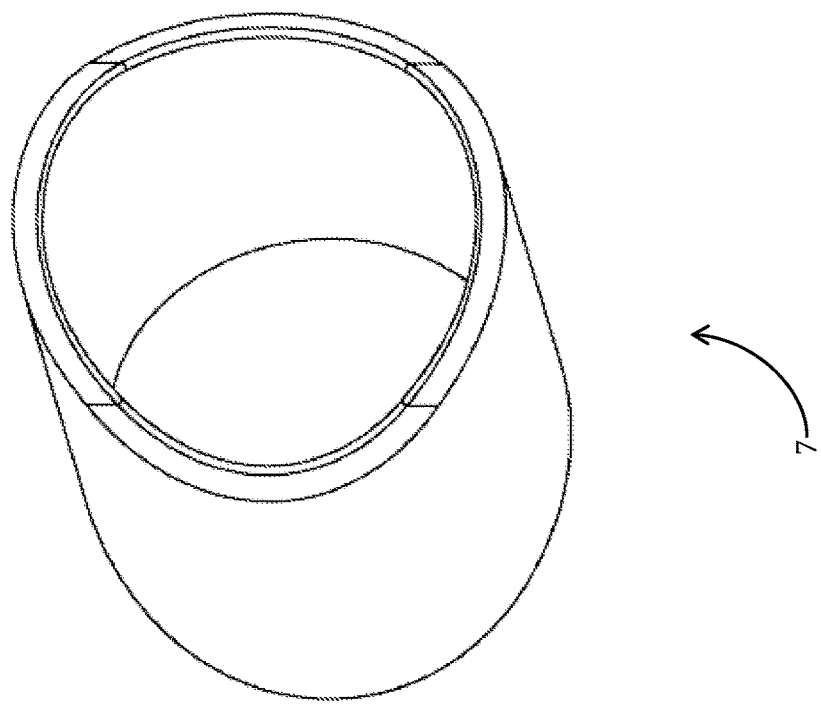
FIG. 18 illustrates a front view of a substantially circular elongate tubing that covers each individual phalange.

A sheath of elongate tubing 7 covers each individual phalange 4 such that the flexible joints of the phalange 4 are exposed. In one embodiment of the subject invention, this tubing 7 is composed of flexible materials. In another embodiment of the subject invention, this tubing 7 is composed of inflexible materials. Accordingly, the plurality of phalanges 4 is covered with a plurality of tubings 7. One embodiment of the tubing 7 is shown in FIGS. 17 and 18. A single flexible tubing (not shown) may cover the entire plurality of phalanges of the clip applier 1.

The distal end 2 of the articulating steerable clip applier 1 contains a final phalange 9. The final phalange 9 has a distal end 10 adapted for coupling to an end effector, such as a surgical jaw assembly 3, and a proximal end 11 that is attached to an adjacent proximal phalange 12. The distal tip 13 of the jaw assembly 3 is a surgical clip applicator for applying a surgical clip to a blood vessel (not shown).

The proximal end of the articulating steerable clip applier 1 contains an initial phalange 14. The initial phalange 14 has a proximal end 101 operatively coupled to a user-operated handle 100 and a distal end 16 that is attached to an adjacent first distal phalange 17.

Figure 11:
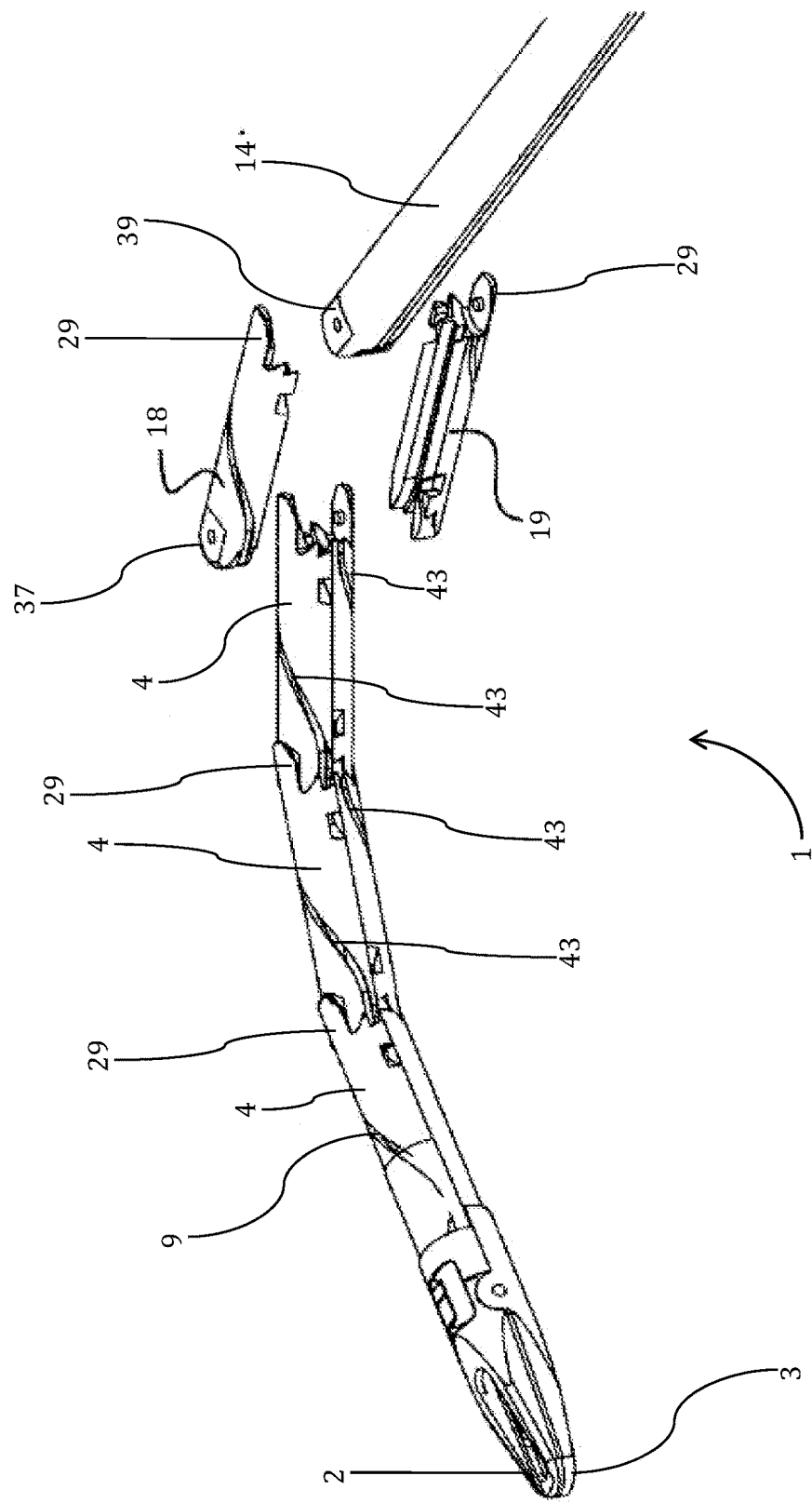
FIG. 11 illustrates a perspective view of the articulating steerable clip applier showing an individual phalange separated into the top and bottom half-phalanges.
Figure 12:
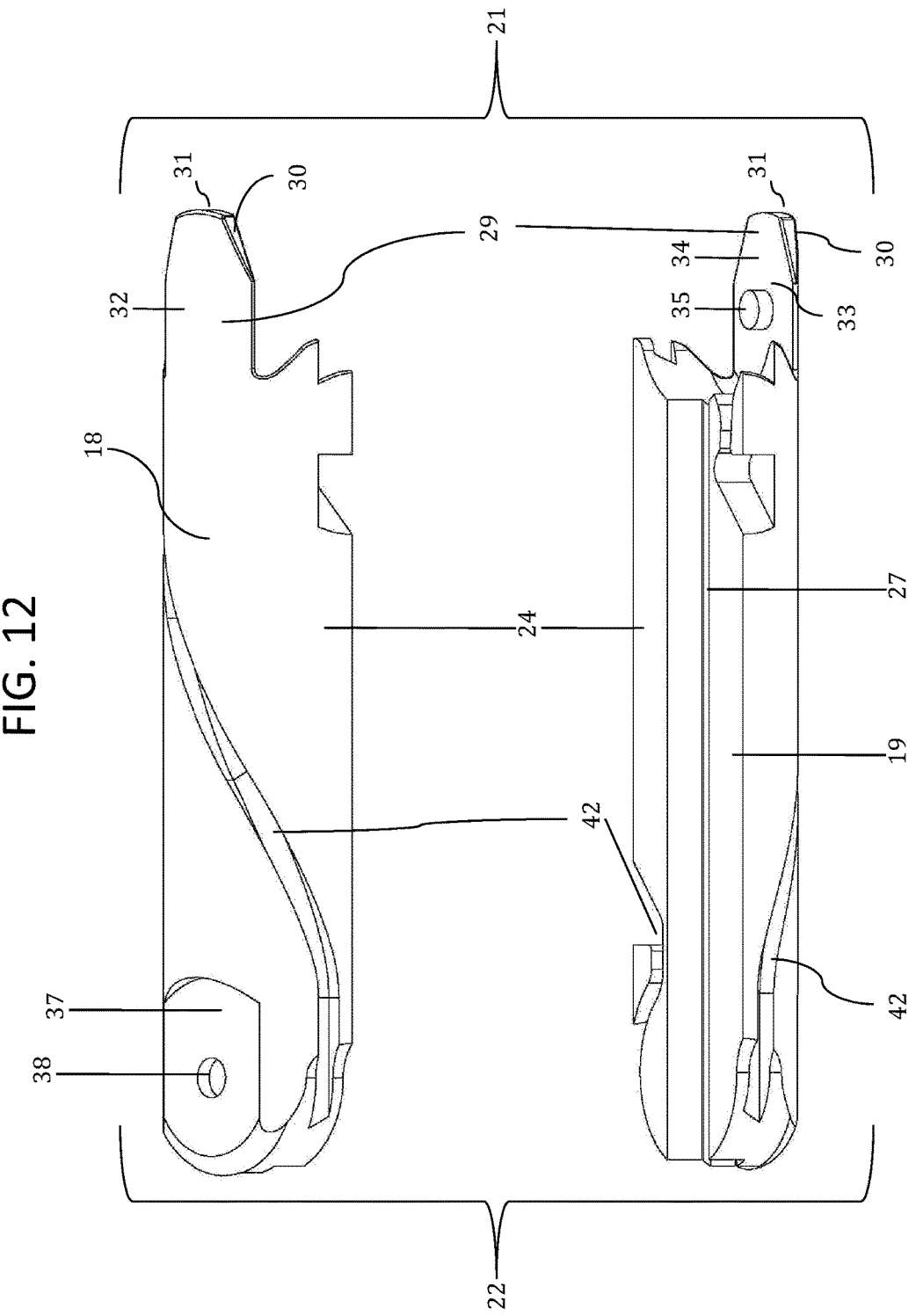
FIG. 12 illustrates a perspective view of a top half-phalange and a bottom half phalange of the articulating steerable clip applier.
Figure 13:
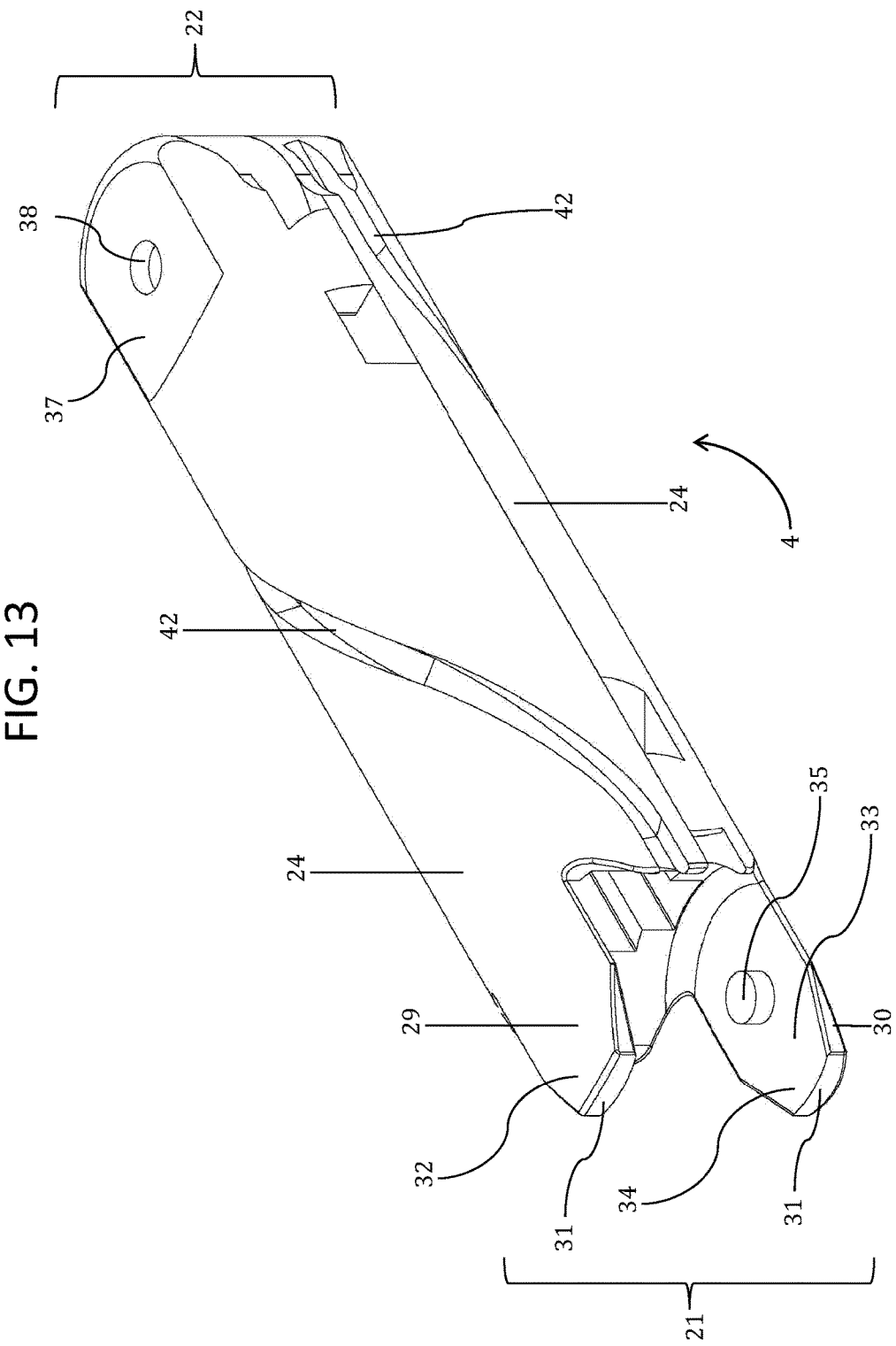
FIG. 13 illustrates a perspective view of a phalange comprising assembled top half and bottom half phalanges of the articulating steerable clip applier.

FIGS. 11-13 illustrate individual phalanges 4 spaced apart, but the phalanges 4 are disposed in the articulating clip applier 1 so that the distal end of each proximal phalange 4 co-acts with the proximal end of the adjacent distal phalange 4.

Each phalange 4 has a generally cylindrical configuration and is symmetrical about a longitudinal axis. Each phalange 4 has an exterior surface 18, described more fully below, and an interior surface 19 that defines a lumen 20 extending between the proximal end 21 and distal end 22. FIG. 10 illustrates a vertical cross-sectional view of an individual phalange 4 at line 18 of FIG. 9. The plurality of lumens 20 of each phalange 4 forms an internal longitudinal passage 23 in the articulating clip applier 1. Longitudinal passage 23 permits actuators, surgical clips, surgical clip carrying assemblies and other functional elements to pass through clip applier 1 and to control the operation of clip movement, clip ligation or phalange articulation. Each phalange 4 is composed of two half phalanges 24. As shown in FIG. 12, each half phalange 24 has the same structure: a curved exterior surface 18 and a generally planar interior surface 19. Each half phalange 24 has a substantially half-round or half-elliptical cross-sectional configuration so that an assembled phalange 4 has a substantially cylindrical configuration. The interior surface 19 of each half phalange 24 contains a longitudinal channel 27.

The proximal end 21 of the exterior surface 18 of each half phalange 24 contains an extension 29. The extension 29 may have angled sides 30 that form a curved end 31. The top surface 32 of each extension 29 has a curvature that is substantially the same as the curvature of the exterior surface 18. The bottom 33 of each extension 29 has a substantially flat planar surface 34. The bottom 34 of each extension 29 further has a substantially cylindrical protrusion 35.

The distal end 22 of each half phalange 24 contains a substantially flat planar surface 37 that is lowered from the curved exterior surface 18. The substantially flat planar surface 37 has a substantially circular internal bore 38 with a diameter that is generally larger than the diameter of the cylindrical protrusion 35.

A phalange 4 is assembled by attaching the interior surfaces 19 of two half phalanges 24 to one another so that the two longitudinal channels 27 on each interior surface 19 of each half phalange 24 form the lumen 20. An assembled phalange 4 will have two extensions 29 on the proximal end 21, with their respective substantially cylindrical protrusions 35 facing each other. The substantially flat planar surfaces 37 of the distal end 22 will be on opposing sides of the assembled phalange 4.

In one embodiment of the subject invention, the phalanges 4 are composed of injected-molded plastic.

As shown in FIGS. 3 and 11, the plurality of phalanges 4 is connected end to end by pivoting links 5 in the following manner:

The initial phalange 14 has a proximal end 101 attached to a user-operated handle 100 (shown in FIG. 19). The distal end 16 of the initial phalange 14 has substantially flat planar surfaces 39 on the top and bottom of the exterior surface 18. The substantially flat planar surfaces 39 each have a substantially circular internal bore 41 with a diameter that is generally larger than the diameter of the cylindrical protrusion 35.

The clip applier 1 is assembled by placing the two substantially cylindrical protrusions 35 on the proximal end 21 of the first distal phalange 17 into the internal bores 41 on opposing sides on the distal end 16 of the initial phalange 14. This pivoting link 5 attaches the first distal phalange 17 to the initial phalange 14.

The proximal end 21 of the first distal phalange 17 may pivot with respect to the initial phalange 14. The two substantially cylindrical protrusions 35 may rotate within the internal bores 41. The substantially flat planar surfaces 34 of each extension 29 rotate freely on the substantially flat planar surfaces 39 on opposing sides of the initial phalange 14.

Second, third and subsequent distal phalanges 4, as desired, are added to the first distal phalange 17 as follows: the two substantially cylindrical protrusions 35 on the proximal end 21 of a subsequent phalange 4 are placed into the internal bores 38 on opposing sides on the distal end 22 of the preceding proximal phalange 4.

As shown in FIGS. 1, 3, 5, 6 and 7, the proximal ends 21 of all subsequent distal phalanges 4 may pivot with respect to distal ends 22 of their respective adjacent proximal phalanges 4. The protrusions 35 on the proximal end 21 of each subsequent distal phalange 4 may rotate within the internal bores 38 on the distal end 22 of the adjacent proximal phalange 4. The substantially flat planar surfaces 34 of each extension 29 rotate freely on the substantially flat planar surfaces 37 of the adjacent proximal phalange 4.

Figure 9:
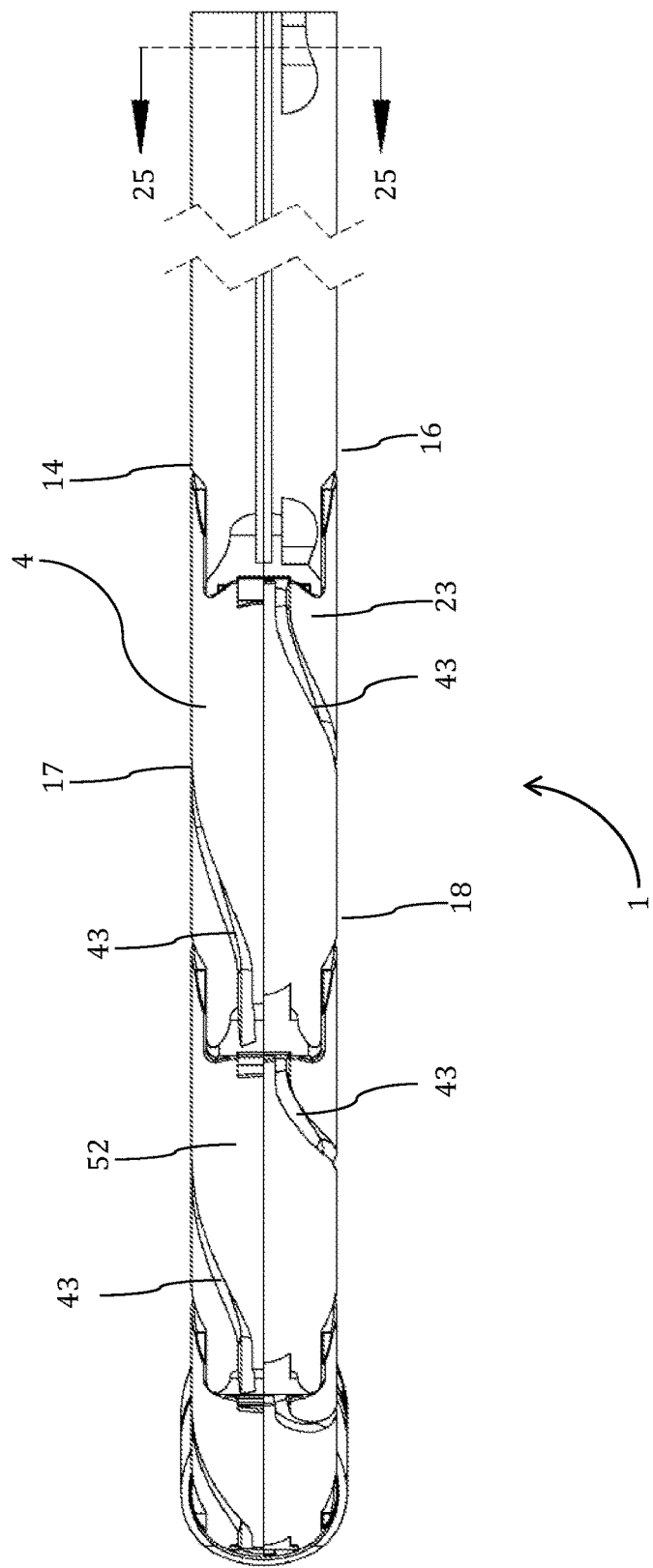
FIG. 9 illustrates a side view of the articulating steerable clip applier showing the opposing spiraled grooves which contain the tension wires.
Figure 10:
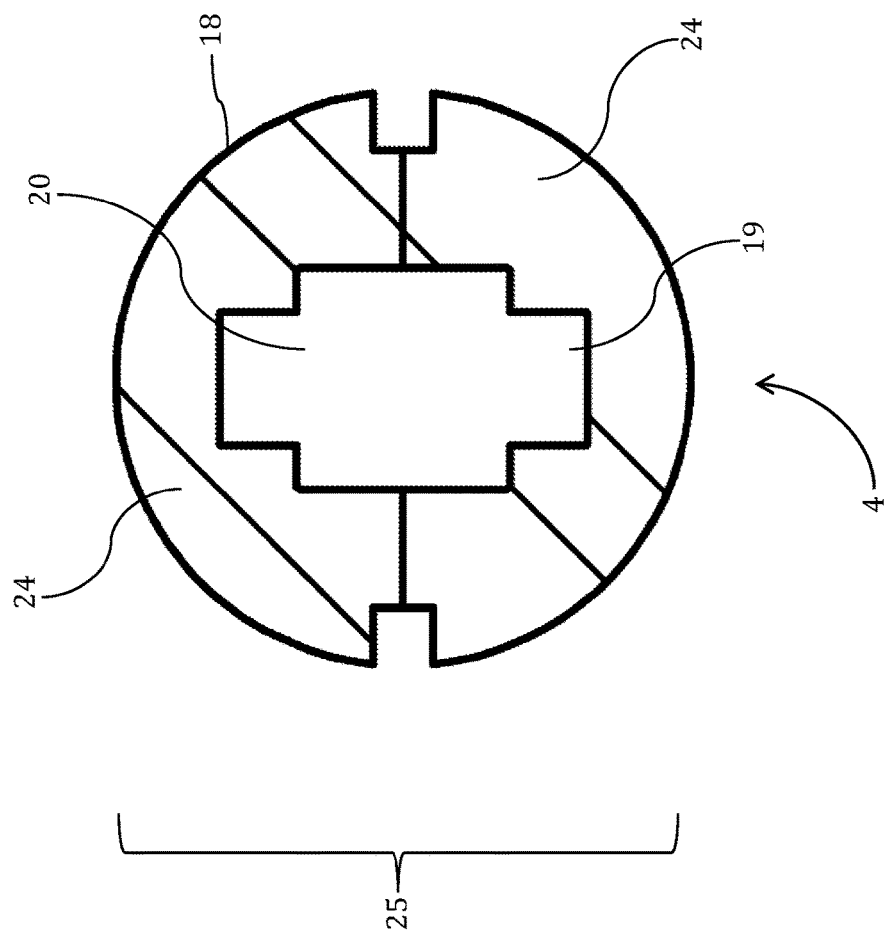
FIG. 10 illustrates a vertical cross-sectional view of an individual phalange at line 18 of FIG. 9 which contains a lumen that allows actuators, surgical clips, surgical clip carrying assemblies and other functional elements to pass through and operate to control clip movement, clip ligation or phalange articulation.

As shown in FIGS. 9, 12 and 13, the exterior surface 18 of each half phalange 24 contains at least one axially extending s-shaped groove 42 or channel. The curve of the s-shaped groove 42 traverses the width and length of the exterior surface 18 of the half phalange 24. The s-shaped groove 42 begins on one side of the exterior surface 18 at the proximal end 21 of the half phalange 24, axially extends and curves over the exterior surface 18 to the opposing side of the exterior surface on the distal end 22 of the half phalange 24.

Once a phalange 4 is assembled, it has two grooves 42 on both exterior surfaces 18 that axially extend in the phalange 4 in opposing s-shaped curves. Once the plurality of phalanges 4 is assembled, the two s-shaped grooves 42 form two continuous axially extending spiral shaped channels 43 that curve in opposing directions from each other.

A tension cable or wire is inserted into each spiral shaped channel 43, to provide steering control for the plurality of phalanges 4. Tension wire is preferably made from a super-elastic material, e.g., nickel titanium alloy, braided stainless steel, a single stainless steel wire, Kevlar, a high tensile strength monofilament thread, or combinations thereof.

Figure 5:
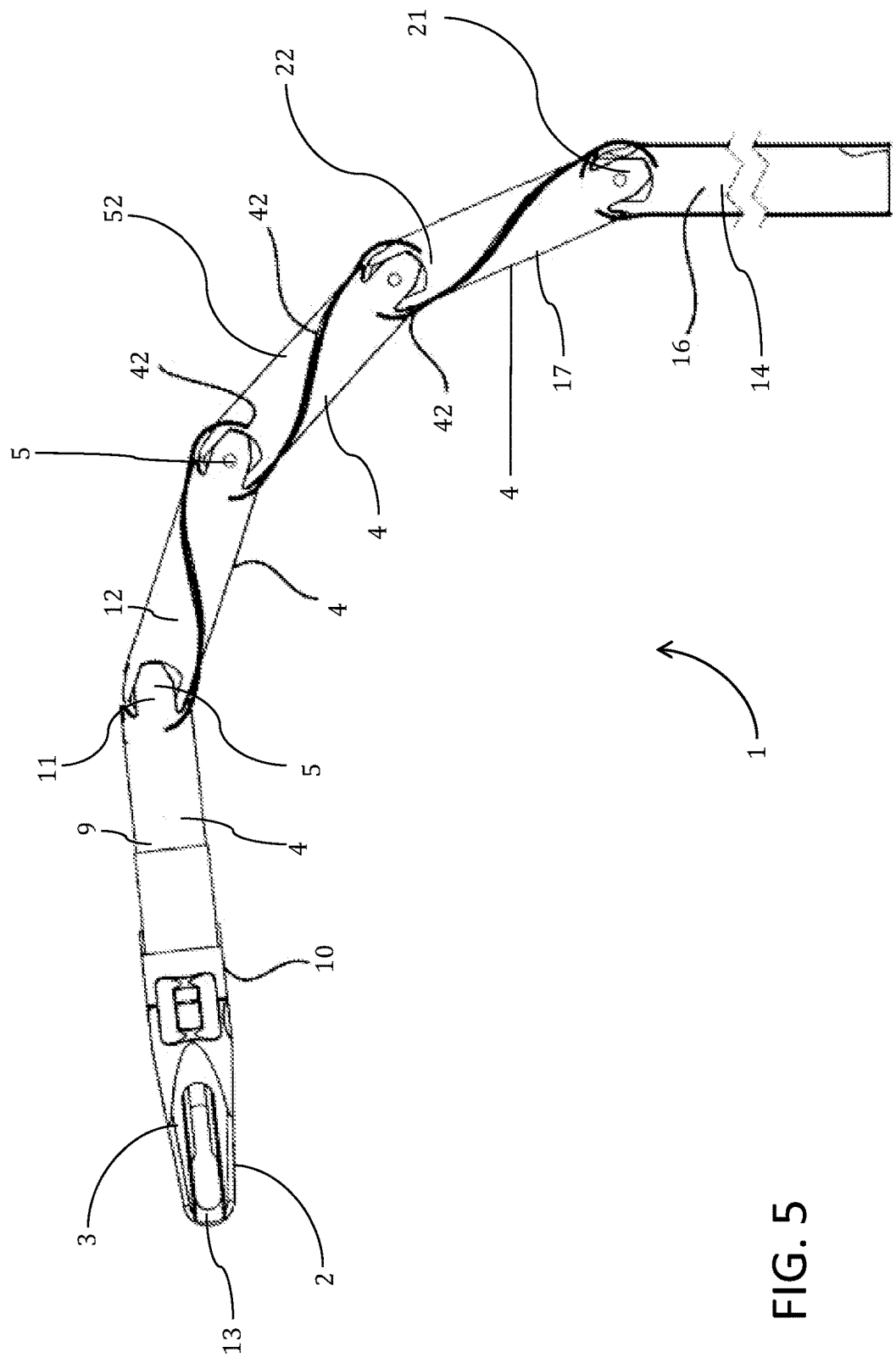
FIG. 5 illustrates another top view of the articulating steerable clip applier showing the separate angles of movement by individual phalanges guided by tension wires connected from a first phalange traversing through opposing spiraled grooves on the next distal phalange to attach to a second distal phalange.
Figure 6:
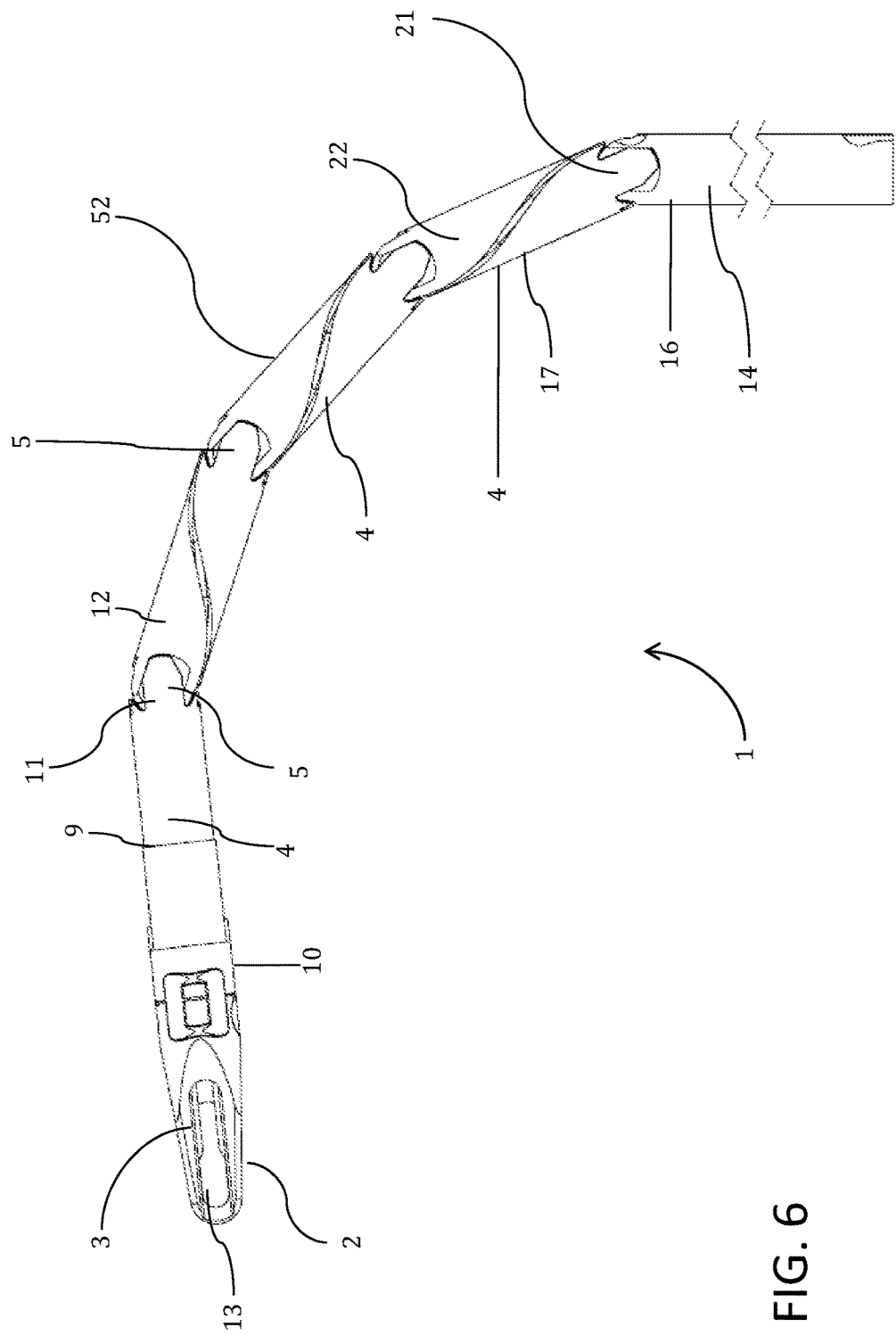
FIG. 6 illustrates another top view of the articulating steerable clip applier showing the separate angles of movement by individual phalanges with opposing spiraled grooves for holding the tension wires.
Figure 7:
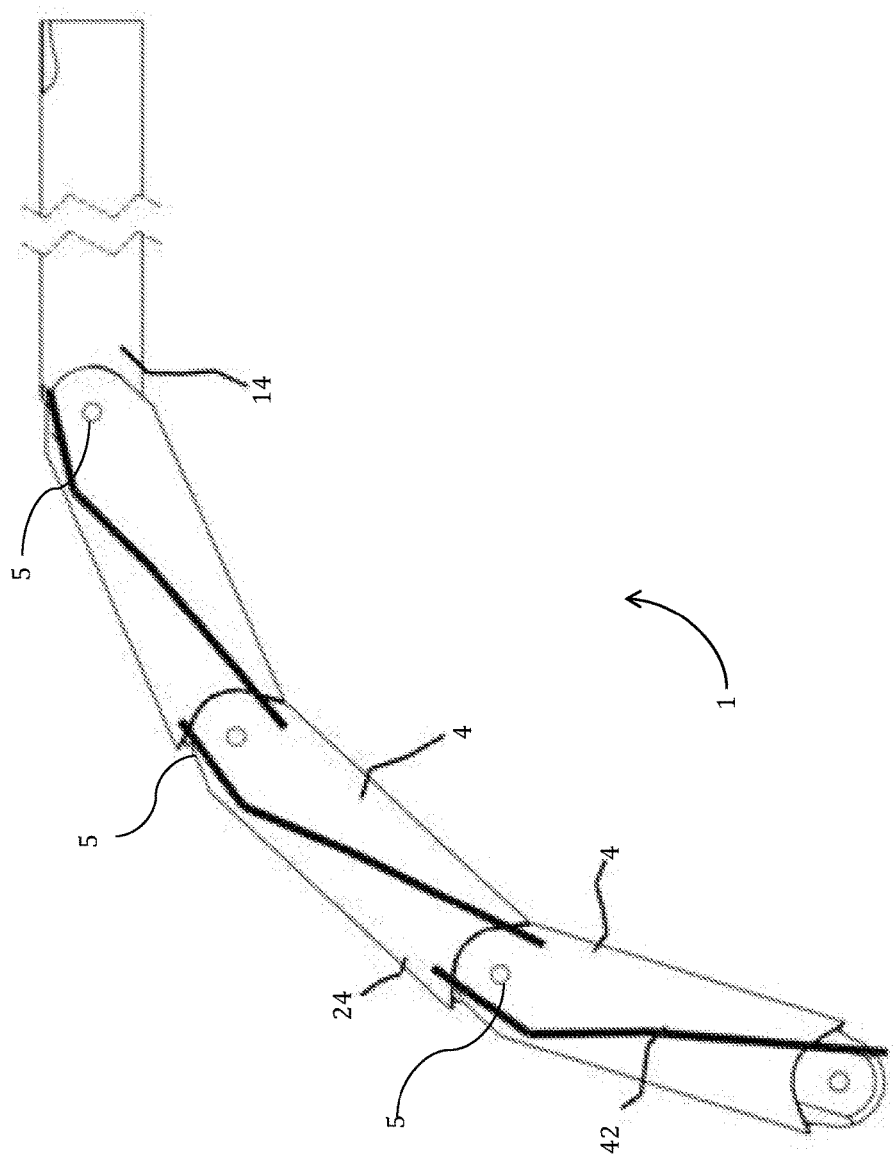
FIG. 7 illustrates a top view of connected adjacent phalanges of the articulating steerable clip applier without covers showing the separate angles of movement by different adjacent phalanges by flexible tension wires.
Figure 8:
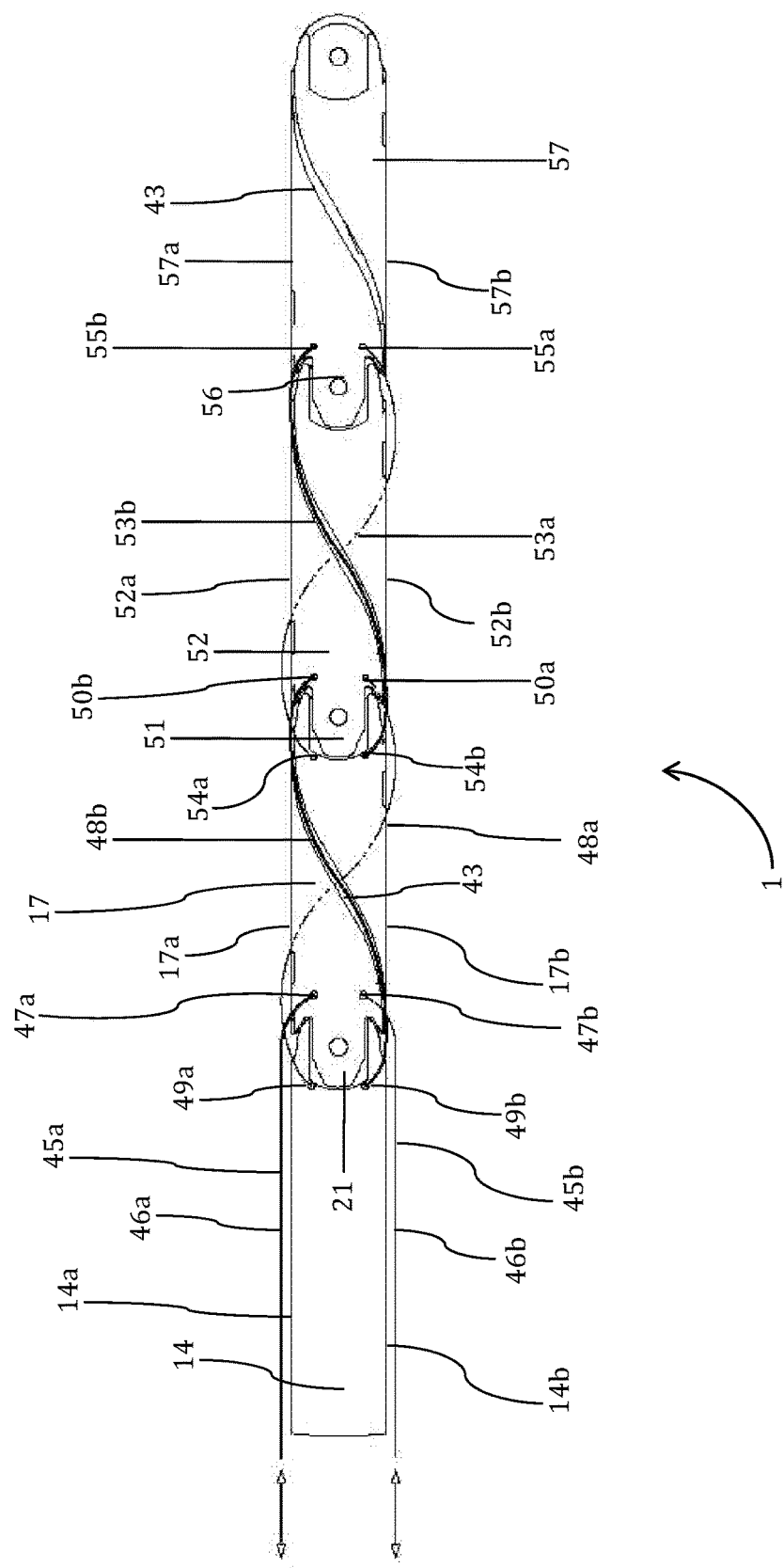
FIG. 8 illustrates the attachments of separate flexible tension wires on the separate phalanges of the articulating steerable clip applier, wherein each tension wire connects on its proximal end to one side of a first phalange, traverses through opposing spiraled grooves on the next distal phalange and attaches on its distal end to the opposing side of a second distal phalange.

As shown in FIGS. 5, 7 and 8 a first set of two wires 45a and 45b are connected on their respective proximal ends 46a and 46b to the initial phalange 14 and connected on their respective distal ends 47a and 47b to the proximal end 21 of the adjacent first distal phalange 17. The proximal end 46a of wire 45a is attached to one side 14a of the initial phalange 14 and the distal end 47a of wire 45a is attached to the side 17a of the first distal phalange 17 on its proximal end 21. The proximal end 46b of wire 45b is attached to the opposing side 14b of the initial phalange 14 and the distal end 47b of wire 45b is attached to the side 17b of the first distal phalange 17 on its proximal end 21. When wire 45a is pulled, this tensile force causes the first distal phalange 17 to pivot back and forth at its proximal end 21 towards side 17a, away from side 14b. When wire 45b is pulled, this tensile force causes the first distal phalange 17 to pivot back and forth at its proximal end 21 towards side 17b, away from side 14a. Furthermore, each subsequently attached phalange 4 is moved by the same pivoted angle above, when either wire 45a or 45b is pulled.

A second set of two wires 48a and 48b are connected on their respective proximal ends 49a and 49b to the initial phalange 14 and connected on their respective distal ends 50a and 50b to the proximal end 51 of the second distal phalange 52, which is adjacent to phalange 17. The wires 48a and 48b are inserted into the two spiral shaped channels 43 that curve in opposing directions. The proximal end 49a of wire 48a is attached to one side 14a of the initial phalange 14 and the distal end 50a of wire 48a is attached to the opposing side 52b of the second distal phalange 52 on its proximal end 51. The proximal end 49b of wire 48b is attached to the opposing side 14b of the initial phalange 14 and the distal end 50b of wire 48b is attached to the opposing side 52a of the second distal phalange 52 on its proximal end 51. When wire 48a is pulled, this tensile force causes the second distal phalange 52 to pivot back and forth at its proximal end 51 towards side 52b, away from side 14a. When wire 48b is pulled, this tensile force causes the second distal phalange 52 to pivot back and forth at its proximal end 51 towards side 52a, away from side 14b. Furthermore, each subsequently attached phalange 4 is moved by the same pivoted angle above, when either wire 48a or 48b is pulled. Since the proximal end and the distal end of each wire 48a or 48b is attached to opposing sides of the initial phalange 14 and the second distal phalange 52, pulling either wire 48a or 48b causes the second distal phalange 52 to pivot in the direction of the distal end of the wire and away from the proximal end of the wire.

A third set of two wires 53a and 53b are connected on their respective proximal ends 54a and 54b to the first distal phalange 17 and connected on their respective distal ends 55a and 55b to the proximal end 56 of the third distal phalange 57, which is adjacent to second distal phalange 52. The wires 53a and 53b are inserted into the two spiral shaped channels 43 that curve in opposing directions. The proximal end 54a of wire 53a is attached to one side 17a of the first distal phalange 17 and the distal end 55a of wire 53a is attached to the opposing side 57b of the third distal phalange 57 on its proximal end 56. The proximal end 54b of wire 53b is attached to the opposing side 17b of the first distal phalange 17 and the distal end 55b of wire 53b is attached to the opposing side 57a of the third distal phalange 57 on its proximal end 56. When wire 53a is pulled, this tensile force causes the third distal phalange 57 to pivot back and forth at its proximal end 56 towards side 57b, away from side 17a. When wire 53b is pulled, this tensile force causes the third distal phalange 57 to pivot back and forth at its proximal end 56 towards side 57a, away from side 17b. Furthermore, each subsequently attached phalange 4 is moved by the same pivoted angle above, when either wire 53a or 53b is pulled. Since the proximal end and the distal end of each wire 53a or 53b is attached to opposing sides of the first distal phalange 17 and the third distal phalange 57, pulling either wire 53a or 53b causes the third distal phalange 57 to pivot in the direction of the distal end of the wire and away from the proximal end of the wire.

Additional sets of two wires may be connected on their proximal ends to a proximal phalange and connected on their distal end to the proximal end of phalange that is two phalanges distal from the proximal phalange. The wires are inserted into the two spiral shaped channels 43 that curve in opposing directions. The proximal end of each wire is attached to one side of the proximal phalange. The distal end of each wire is attached to the opposing side of the phalange that is two phalanges distal from the proximal phalange. When each wire is pulled, this tensile force causes the phalange that is two phalanges distal from the proximal phalange to pivot back and forth at its proximal end. The direction of this pivoting is towards the distal end attachment of each wire and away from the proximal end attachment of each wire.

A user may actuate the wires above to pivot all the remaining phalanges 4 such that the angle 6 between the distal end of a preceding phalange and the proximal end of the subsequent phalange in the clip applier is substantially equivalent. FIGS. 1 and 2 illustrate the separate, but identical, angles of movement 6 by individual phalanges 4.

As each individual phalange 4 pivots by an equivalent angle 6, the sum of these angles 6 causes the distal end 2 of the clip applier 1 to pivot by a large angle or a cascading actuation effect, as shown in FIG. 1.

Figure 14:
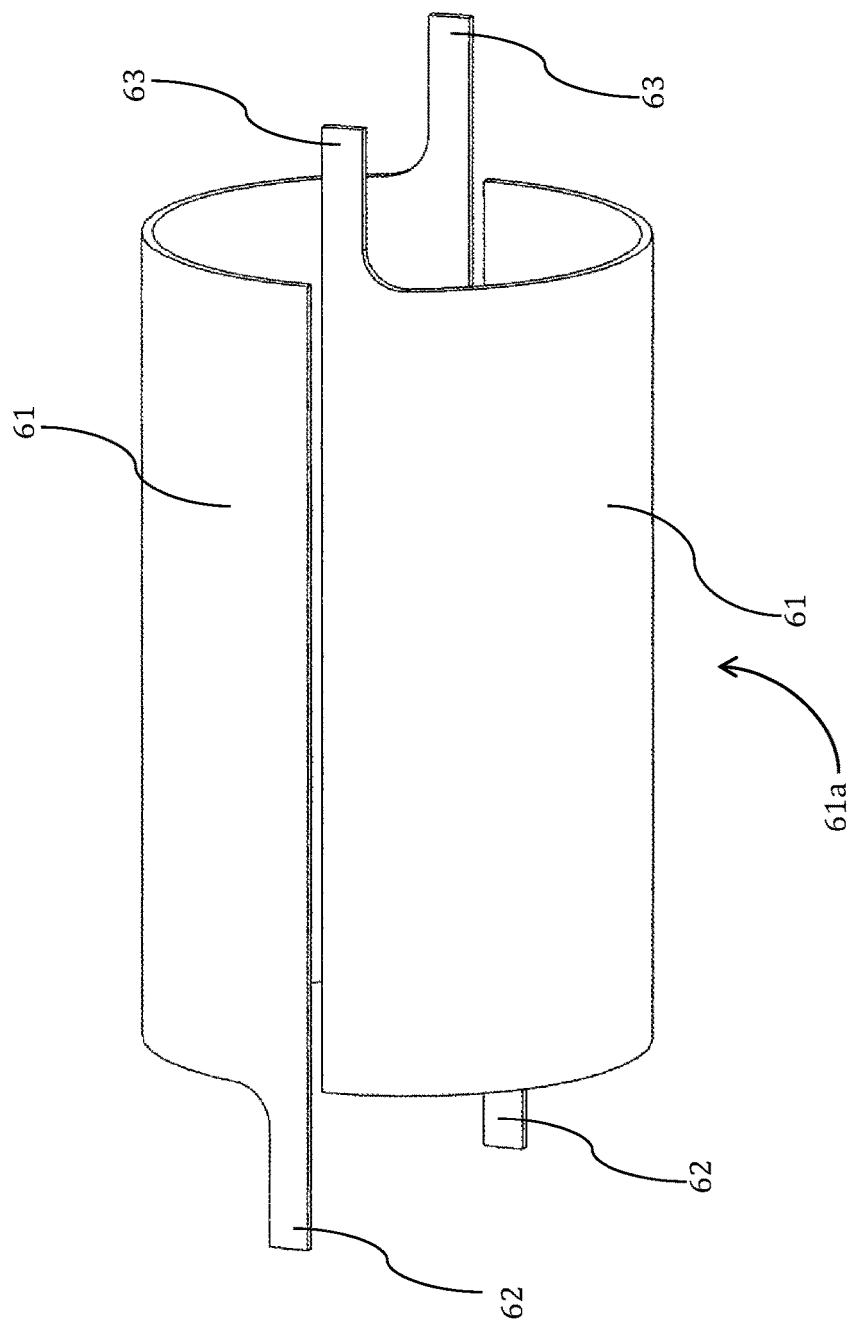
FIG. 14 illustrates a side view of a top and bottom semi-circular connecting ligaments of an individual phalange.
Figure 15:
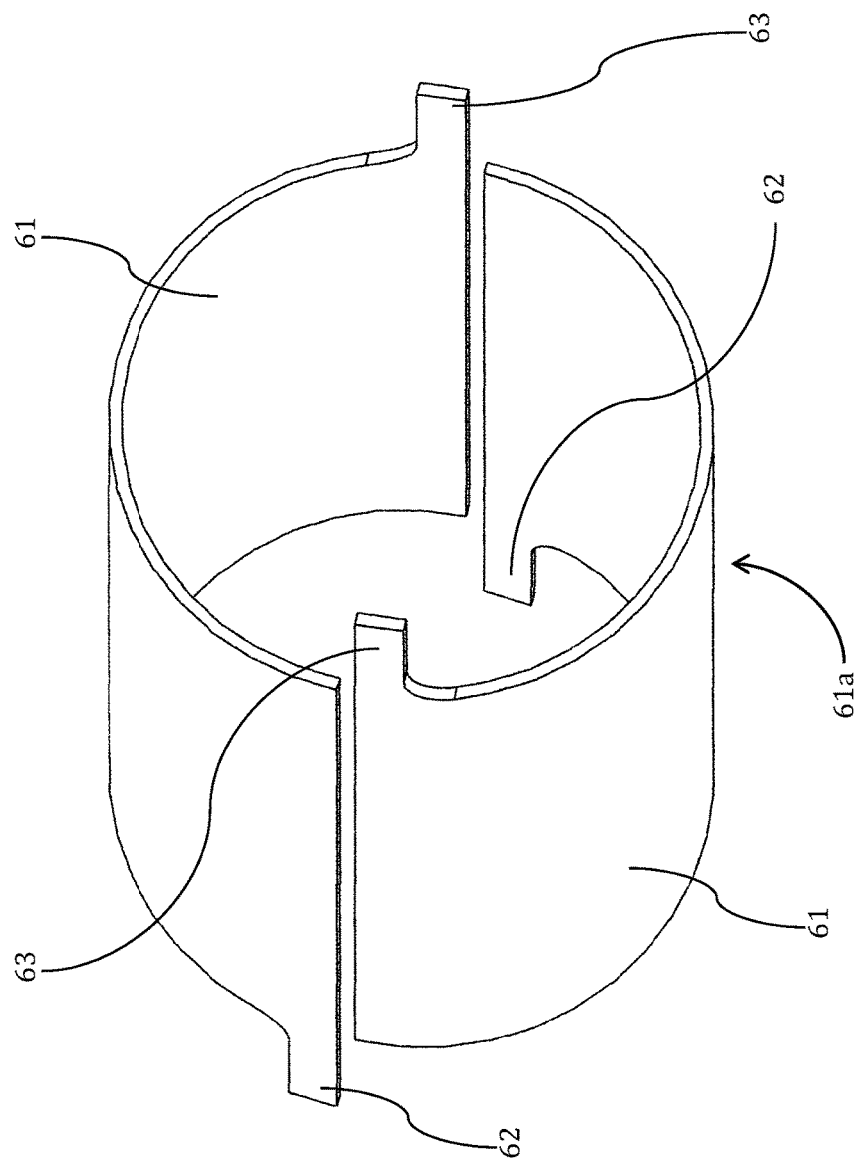
FIG. 15 illustrates a front view of a top and bottom semi-circular connecting ligaments of an individual phalange.
Figure 16:
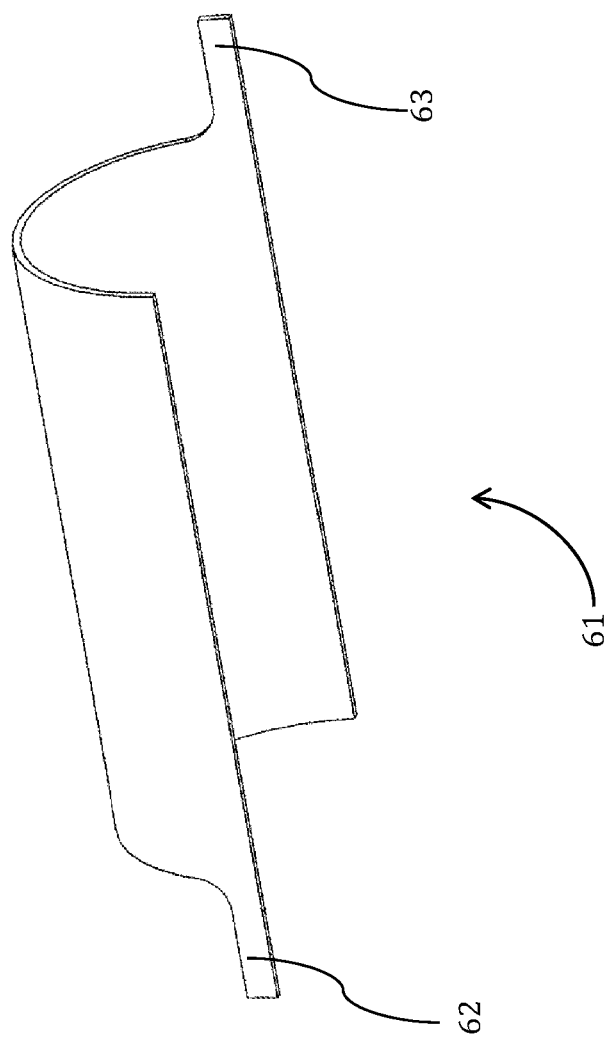
FIG. 16 illustrates a side view of a top semi-circular connecting ligament of an individual phalange.

In another embodiment of the subject invention, as shown in FIGS. 14-16, the tension wires above may be replaced by semi-circular connecting ligaments 61. Each individual phalange 4 may be substantially covered with two semi-circular connecting ligaments 61. FIGS. 14 and 15 illustrate two semi-circular connecting ligaments 61 in an opposing top-bottom configuration 61a to cover an individual phalange (not shown).

Each semi-circular connecting ligament 61 has a flexible tip 62 on its proximal end and a flexible tip 63 on its distal end. Furthermore, flexible tips 62 and 63 are on opposing sides of each semi-circular connecting ligament 61.

In the opposing top-bottom configuration 61a, flexible tips 62 are attached to the distal end of a proximal phalange on opposing sides, an adjacent distal phalange is substantially covered by the two opposing semi-circular connecting ligaments 61, and flexible tips 63 are attached to the proximal end of a second distal phalange on opposing sides.

Each flexible tip 62 is attached to one side of the proximal phalange and each flexible tip 63 is attached to the opposing side of the second distal phalange. When a flexible tip 62 is pulled, this force causes the second distal phalange to pivot at its proximal end. The direction of this pivoting is away from the flexible tip 62 that is pulled.

A user may actuate the flexible tips 62 above to pivot all the remaining phalanges 4 such that the angle 6 between the distal end of a preceding phalange and the proximal end of the subsequent phalange in the clip applier is substantially equivalent. FIGS. 1 and 2 illustrate the separate, but identical, angles of movement 6 by individual phalanges 4.

In one embodiment of the subject invention, the narrow plurality of phalanges 4 may easily fit within respective envelopes of 10 mm and 3 mm MIS instrumentation, while retaining flexible movements within a patient.

What is claimed is:

1. A device comprising:
   a handle;
   a first phalanx movably coupled to the handle;
   an intermediate phalanx movably coupled to the first phalanx;
   a final phalanx movably coupled to the intermediate phalanx; and
   a tension wire extending from the handle and operably coupled to the first phalanx, the tension wire configured to allow a user-applied motion applied to the handle to change tension in the tension wire to move the first phalanx in a first direction, the movement of the first phalanx in the first direction further configured to move the intermediate phalanx and the final phalanx in the first direction in response to the motion of the first phalanx, wherein the tension wire is a first tension wire and the user-applied motion is a first user-applied motion, the device further comprising: a second tension wire extending from the handle and operably coupled to the first phalanx, the second tension wire configured to allow a second user-applied motion applied to the handle to change tension in the second tension wire to move the first phalanx in a second direction, the movement of the first phalanx in the second direction further configured to move the intermediate phalanx and the final phalanx in the second direction in response to the motion of the first phalanx, wherein each of the first phalanx, the intermediate phalanx, and the final phalanx comprises two s-shaped grooves on opposite sides of an exterior surface of the phalanx, the two s-shaped grooves forming two continuous axially extending spiral-shaped channels when the first phalanx, the intermediate phalanx, and the final phalanx are coupled.

2. The device of claim 1, wherein the intermediate phalanx moves at a same angle and in a same direction as the first phalanx, wherein the angle of the first phalanx is measured from the handle to the first phalanx, and the angle of the intermediate phalanx is measured from the first phalanx to the intermediate phalanx.

3. The device of claim 1, wherein a third user-applied motion applies a first amount of force to the first tension wire and a second amount of force to the second tension wire, the two amounts of force combining to move the first phalanx in a third direction.

4. The device of claim 1, wherein the tension wires are disposed within the s-shaped grooves, the first tension wire connected to the handle, extending through one of the s-shaped channel on the first phalanx, and connecting to the intermediate phalanx, and the second tension wire connected to the handle, extending through the other of the s-shaped channels on the first phalanx, and connecting to the intermediate phalanx.

5. The device of claim 4, further comprising:
a third tension wire attached to the first phalanx in the s-shaped channel containing the first tension wire, extending through one of the s-shaped channels on the intermediate phalanx, and connected to the final phalanx; and
a fourth tension wire attached to the first phalanx in the other s-shaped channel containing the second tension wire, extending through the other of the s-shaped channels on the intermediate phalanx, and connected to the final phalanx.

6. The device of claim 5, wherein tension on the first tension wire moves the first phalanx in a first direction, the motion in the first direction imparting tension on the third tension wire, the tension in the third tension wire moving the intermediate phalanx in the first direction; and wherein tension on the second tension wire moves the first phalanx in a second direction, the motion in the second direction imparting tension on the fourth tension wire, the tension in the fourth tension wire moving the intermediate phalanx in the second direction.

7. A device comprising:
a handle;
at least two tension wires;
a first phalanx operably coupled to the handle and further connected to the handle via two tension wires, wherein a user-applied motion applied to the handle changes tension in at least one of the two tension wires, wherein the tension in the at least one tension wire moves the first phalanx;
at least one intermediate phalanx, the first intermediate phalanx connected to the first phalanx via a connector, and wherein each phalanx is connected via a substantially similar connector to a successive phalanx; and
an end effector coupled to a final intermediate phalanx;
wherein the at least one intermediate phalanx, the final phalanx, and the end effector move in response to the motion of the first phalanx;
wherein each phalanx comprises two s-shaped grooves on opposite sides of an exterior surface of the phalanx, wherein the s-shaped grooves begin on a first side of a proximal end of the exterior surface and curve over the exterior surface to an opposing side of a distal end of the exterior surface.

8. The device of claim 7, wherein each of the first phalanx, at least one intermediate phalanx, and the final phalanx comprises a lumen, and the lumen from the first phalanx, the at least one intermediate phalanx, and the final phalanx, when connected, form an internal longitudinal passage.

9. The device of claim 7, wherein the s-shaped grooves form two continuous axially extending spiral shaped channels, each continuous axially extending spiral shaped channel extends along the first phalanx, the at least one intermediate phalanx, and the final phalanx.

10. The device of claim 9, wherein the axially extending spiral shaped channels curve in opposing directions.

11. The device of claim 10, wherein a tension wire is disposed within each s-shaped channel, and wherein tension applied to at least one of the tension wires in the s-shaped channels provides steering control of the phalanx.

12. The device of claim 11, wherein the two tension wires are attached to the handle and are each disposed within one of the s-shaped channels on the first phalanx, and are attached in opposing s-shaped channels of a first intermediate phalanx;
wherein applying tension to a first of the two tension wires moves the first phalanx in a first direction;
wherein applying tension to a second of the two tension wires moves the first phalanx in a second direction;
wherein the first direction and the second direction are defined by a pivot angle, wherein the pivot angle is the angle between the handle to the first phalanx.

13. The device of claim 12, wherein each intermediate phalanx is connected to the previous and successive phalanx via two tension wires, wherein motion of the first phalanx applies tension to tension wires around the first intermediate phalanx and the tension pivots the first intermediate phalanx in the first or second direction such that the angle between the first intermediate phalanx and the successive phalanx is the same as the pivot angle between the handle and the first phalanx.

14. The device of claim 13, wherein the first phalanx is connected to the first intermediate phalanx and second intermediate phalanx from the at least one intermediate phalanx via a phalanx-wire connection, wherein the phalanx-wire connection comprises two phalanx tension wires;
wherein the first of the two phalanx tension wires is connected to and disposed within a proximal end of a first of the s-shaped channels of the first phalanx and wherein the second of the two phalanx tension wires is connected to and disposed within a proximal end of the second of the s-shaped channels of the first phalanx;
wherein the two phalanx tension wires are each disposed within one of the s-shaped channels of the first intermediate phalanx; and
wherein the first of the two phalanx tension wires is connected to and disposed within a distal end of a first of the s-shaped channels of the second intermediate phalanx and wherein the second of the two phalanx tension wires is connected to and disposed within a distal end of a second of the s-shaped channels of the second intermediate phalanx.

15. The device of claim 14, wherein each phalanx of the intermediate phalanxes is connected to the previous and next phalanx using the phalanx-wire connection, and wherein the final phalanx is secured using two final tension wires, wherein the final tension wires are similarly connected to the proximal end of the penultimate phalanx, are disposed within the two s-shaped channels of the final phalanx, and connected to opposite ends of the end effector.

16. The device of claim 15, wherein the motion of the first phalanx caused by tension on the at least one tension wire causes tension on the at least two phalanx tension wires between the first phalanx and second intermediate phalanx, and the first intermediate phalanx is pivoted by a phalanx pivot angle,
wherein the phalanx pivot angle is the angle between the first phalanx and the first intermediate phalanx, and
wherein the phalanx pivot angle is the same angle as the pivot angle between the handle and the first phalanx.

17. A device comprising:
a handle;
a first phalanx movably coupled to the handle;

an intermediate phalanx movably coupled to the first phalanx;

a final phalanx movably coupled to the intermediate phalanx;

a first pair of tension wires extending from the handle and operably coupled to the first phalanx, the first pair of tension wires configured to allow user-applied motion applied to the handle to change tension in the tension wire to move the first phalanx to a specified angle based on the user-applied motion;

a second pair of tension wires extending from the first phalanx and operably coupled to the intermediate phalanx, the second pair of tension wires configured to move the intermediate phalanx at the specified angle in response to the motion of the first phalanx;

a third pair of tension wires expending from the intermediate phalanx to the final phalanx, the third pair of tension wires configured to move the final phalanx at the specified angle in response to motion of the intermediate phalanx; and an end effector operably coupled to the final phalanx, the end effector configured to perform a function in response to a second user-applied motion applied to the handle;

wherein the first pair of tension wires are coupled to the first phalanx through an s-shaped channel on the first phalanx and connected to the handle and the intermediate phalanx, the second pair of tension wires are coupled to the first intermediate phalanx through an s-shaped channel on the intermediate phalanx and are connected to the first phalanx and the final phalanx, and the third pair of tension wires are coupled to the final phalanx through an s-shaped channel on the final phalanx and are connected to the intermediate phalanx and the end effector.

* * * * *

UNITED STATES PATENT AND TRADEMARK OFFICE
CERTIFICATE OF CORRECTION

PATENT NO. : 9,918,715 B2
APPLICATION NO. : 14/339021
DATED : March 20, 2018
INVENTOR(S) : Pavel Menn Page 1 of 1

It is certified that error appears in the above-identified patent and that said Letters Patent is hereby corrected as shown below:

In the Claims

Column 13, Line 7, please replace "channel" with "channels"
Column 15, Line 16, please replace "expending" with "extending"

Signed and Sealed this
Twenty-ninth Day of January, 2019

Andrei Iancu
*Director of the United States Patent and Trademark Office*